United States Patent [19]

Petrzilka et al.

[11] Patent Number: 4,915,480
[45] Date of Patent: Apr. 10, 1990

[54] LIQUID CRYSTALLINE COMPOUNDS AND MIXTURES

[76] Inventors: Martin Petrzilka, 54 Schwartzackerstrasse, CH-4303 Kaiseraugst; Martin Schadt, 77 Liestalerstrasse, CH-4411 Seltisberg; Alois Villiger, 5 Im Ettingerhof, CH-4055 Basel, all of Switzerland

[21] Appl. No.: 218,752
[22] Filed: Jul. 13, 1988

Related U.S. Application Data

[60] Division of Ser. No. 36,132, Apr. 3, 1987, which is a continuation of Ser. No. 735,507, May 20, 1985, abandoned.

[30] Foreign Application Priority Data

May 25, 1984 [CH] Switzerland .......................... 2571/84
Mar. 12, 1985 [CH] Switzerland .......................... 1113/85

[51] Int. Cl.$^4$ ...................... G02F 1/13; C07C 161/04; C07D 239/26; C07D 319/06; C09K 19/34; C09K 19/30
[52] U.S. Cl. .............................. 350/350 R; 252/299.5; 252/299.6; 252/299.61; 252/299.63; 252/299.66; 350/350 S; 544/335; 544/242; 549/370; 549/373
[58] Field of Search ...................... 252/299.61, 299.63, 252/299.66, 299.5, 299.6; 350/350 R, 350 S; 558/17; 544/335, 242, 296; 549/370, 373

[56] References Cited

U.S. PATENT DOCUMENTS

| | | | |
|---|---|---|---|
| 3,925,444 | 12/1975 | Boller et al. | 252/299.67 |
| 3,947,375 | 3/1976 | Gray et al. | 252/299.66 |
| 3,997,536 | 12/1976 | Boller et al. | 252/299.61 |
| 4,261,651 | 4/1981 | Gray et al. | 252/299.61 |
| 4,512,636 | 4/1985 | Andrews et al. | 252/299.63 |
| 4,528,114 | 7/1985 | Petrzilka et al. | 252/299.61 |
| 4,528,116 | 7/1985 | Dabrowski et al. | 252/299.63 |
| 4,565,425 | 1/1986 | Petrzilka et al. | 252/299.61 |
| 4,621,901 | 11/1986 | Petrzilka et al. | 252/299.63 |
| 4,629,581 | 12/1986 | Boller et al. | 252/299.63 |
| 4,630,896 | 12/1986 | Petrzilka et al. | 252/299.63 |
| 4,676,604 | 6/1987 | Petrzilka | 252/299.63 |
| 4,676,924 | 6/1987 | Dabrowski et al. | 252/299.61 |
| 4,709,030 | 11/1987 | Petrzilka et al. | 252/299.63 |
| 4,770,503 | 9/1988 | Buchecker et al. | 252/299.63 |

FOREIGN PATENT DOCUMENTS

| | | | |
|---|---|---|---|
| 127883 | 3/1984 | European Pat. Off. | |
| 168683 | 1/1986 | European Pat. Off. | 252/299.61 |
| 170082 | 2/1986 | European Pat. Off. | 252/299.61 |
| 227004 | 7/1987 | European Pat. Off. | 252/299.63 |
| 3500909 | 7/1986 | Fed. Rep. of Germany | 252/299.61 |
| 3545345 | 7/1987 | Fed. Rep. of Germany | 252/299.63 |
| 59-199649 | 11/1984 | Japan | 252/299.66 |
| 60-112723 | 6/1985 | Japan | 252/299.63 |
| 60-136555 | 7/1985 | Japan | 252/299.63 |
| 60-146868 | 8/1985 | Japan | 252/299.63 |
| 60-204781 | 10/1985 | Japan | 252/299.61 |
| 60-222458 | 11/1985 | Japan | 252/299.63 |
| 61-00289 | 1/1986 | Japan | |
| 61-27931 | 2/1986 | Japan | 252/299.66 |
| 61-43172 | 3/1986 | Japan | 252/299.61 |

| | |
|---|---|
| 1099767 | 12/1966 United Kingdom . |
| 1099768 | 12/1966 United Kingdom . |

OTHER PUBLICATIONS

Dabrowski et al., Mol. Crystl. Liq. Crystl., vol. 87:109–135 (1982).
Petrzilka, M., Mol. Cryst. Liq. Cryst., vol. 131, pp. 109–123 (10/85).
Baran, J. W., et al., Mol. Cryst. Liq. Crystl., vol. 123, pp. 237–245 (1985).
Dabrowski, R. et al., vol. 124, pp. 241–257, Mol. Cryst. Liq. Cryst., (1985).
Petrzilka, M., et al., vol. 131, pp. 327–342, Mol. Cryst. Liq. Cryst. (12/1985).
Petrzilka, M., Mol. Cryst. Liq. Cryst., vol. 111, pp. 329–346 (1984).
Schadt, M., et al., Abstract G52, the Tenth International Liquid Crystal Conf., York, UK (15–21, Jul. 1984).
Schadt, M., et al., Eurodisplay '84, Proceedings of the Fourth Display Research Conference See, Paris, pp. 53–56 (9/18–20/84).
Dabrowski, R., et al., Abstract I19, the Tenth International Liquid Crystal Conf., York, UK (15–21 Jul. 1984).

Primary Examiner—Teddy S. Gron

[57] ABSTRACT

This invention concerns compounds of the formula:

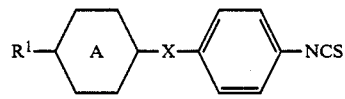

I wherein
X is a single covalent bond, —CH$_2$CH$_2$—, 1,4-phenylene, a 2,5-disubstituted pyrimidine ring or a group of the formula:

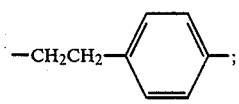

IA

—CH$_2$CH$_2$—⟨⟩—;

ring A is trans-1,4-cyclohexylene or, when X is a single covalent bond, ring A may also be 1,4-phenylene, a 2,5-disubstituted pyrimidine ring or a trans-2,5-disubstituted m-dioxane ring; and
R$^1$ is straight-chain trans-1-alkenyl having 2 to 12 carbon atoms or straight-chain trans-3-alkenyl having 4 to 12 carbon atoms or, when X is —CH$_2$CH$_2$—, R$^1$ may also be 1,4-phenylene, a 2,5-disubstituted pyrimidine ring or a group of formula IA or when ring A is a 2,5-disubstituted pyrimidine ring or a trans-2, 5-disubstituted m-dioxane ring, R$^1$ may also be straight-chain alkyl with 1 to 12 carbon atoms; and one of the benzene rings may have a lateral fluorine substituent;

their manufacture, and liquid crystalline mixtures and electro-optical devices containing same.

9 Claims, No Drawings

LIQUID CRYSTALLINE COMPOUNDS AND MIXTURES

This is a division, of application Ser. No. 36,132 filed Apr. 3, 1988, which is a continuation of Ser. No. 735,507, filed May 20, 1985, now abandoned.

BACKGROUND OF THE INVENTION

1. Field of the Invention

The present invention is concerned with novel phenyl isothiocyanates their method of manufacture as well as liquid crystalline mixtures and electro-optical devices containing same.

2. Background Description

Liquid crystals have recently gained considerable importance as dielectrics in indicating devices, since the optical properties of such substances can be influenced by an applied voltage. Electro-optical devices based on liquid crystals are well known to the person skilled in the art and can be based on various effects such as, for example, the dynamic scattering, the deformation of aligned phases (DAP type) the Schadt-Helfrich effect (rotation cell), the guest/host effect or a cholesteric-nematic phase transition (phase change effect).

Liquid crystals must, however, satisfy a number of requirements in order to be suitable as dielectrics for electro-optical indicating devices. For example, they must have a good chemical stability towards environmental factors such as e.g. heat, moisture, air electromagnetic radiation in the infra-red, visible and ultra-violet region. Further, they should be colourless, should have short response times and not too high a viscosity, should give a good contrast and should have a nematic or cholesteric mesophase in all temperature ranges in which the liquid crystal cell is to be operated. Other properties must fulfill different conditions depending on the type of cell which is used, for example liquid crystals which are used in rotation cells should have a large positive anisotropy of the dielectric constants ($\Delta\epsilon = \epsilon_\parallel - \epsilon_\perp > 0$, $\epsilon_\parallel$ signifying the dielectric constant along the longitudinal axis of the molecule and $\epsilon_\perp$ signifying the dielectric constant perpendicular thereto) and liquid crystals which are used in guest/host cells should have a large positive or negative anisotropy of the dielectric constants. Moreover, in both cases a low threshold potential and a conductivity which is as small as possible are desirable.

Since, in general, it is not possible to achieve all desired and to some extent conflicting properties with a single compound, attempts have mainly been made to optimize the properties for the particular applications by mixing several components. In this case it is, however, important that the components undergo no chemical reactions with one another and have a good miscibility with one another. Further, the mixtures formed should have no smectic mesophases, at least at temperatures at which the liquid crystal cells are to be operated.

SUMMARY OF THE INVENTION

The present invention concerns novel liquid crystalline compounds namely phenyl isothiocyanates of the formula:

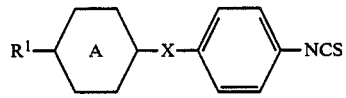

I wherein X represents a single covalent bond, the ethylene group —CH$_2$CH$_2$—, 1,4-phenylene, a 2,5-disubstituted pyrimidine ring or the group of the formula:

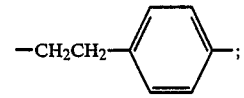

IA ring A represents trans-1,4-cyclohexylene or, when X represents a single covalent bond, also 1,4-phenylene, a 2,5-disubstituted pyrimidine ring or a trans-2,5-disubstituted m-dioxane ring; and R$^1$ signifies straight-chain trans-1-alkenyl with 2 to 12 carbon atoms or straight-chain trans-3-alkenyl with 4 to 12 carbon atoms or, when X represents —CH$_2$CH$_2$—, 1,4-phenylene, a 2,5-disubstituted pyrimidine ring or a group of formula IA or ring A denotes a 2,5-disubstituted pyrimidine ring or a trans-2,5-disubstituted m-dioxane ring, R$^1$ also signifies straight-chain alkyl with 1 to 12 carbon atoms; and one of the benzene rings present in formula I optionally has a lateral fluorine substituent.

The invention is also concerned with the manufacture of the compounds of formula I above, liquid crystalline mixtures which contain compounds of formula I above as well as their use for electro-optical purposes.

DETAILED DESCRIPTION OF THE INVENTION

The present invention concerns a liquid crystalline compound of the formula:

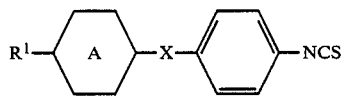

I wherein

X is a single covalent bond, —CH$_2$CH$_2$—, 1,4-phenylene, a 2,5-disubstituted pyrimidine ring or a group of the formula:

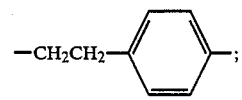

IA ring A is a trans-1,4-cyclohexylene or, when X is a single covalent bond, ring A may also be 1,4-phenylene, a 2,5-disubstituted pyrimidine ring or a trans-2,5-disubstituted m-dioxane ring; and R$^1$ is straight-chain trans-1-alkenyl having 2 to 12 carbon atoms or straight-chain trans-3-alkenyl having 4 to 12 carbon atoms or, when X is —CH$_2$CH$_2$—, 1,4-phenylene, a 2,5-disubstituted pyrimidine ring or a group of formula IA or when ring A is a 2,5-disubstituted pyrimidine ring or a trans-2,5-disubstituted m-dioxane ring, R$^1$ may also be straight-chain alkyl with 1 to 12 carbon atoms; and one of the benzene rings may have a lateral fluorine substituent.

In particular, the compounds of formula I in accordance with the invention give steep transmission curves and short switching times when used in electro-optical devices. Moreover, the phenyl isothiocyanates in accordance with the invention have low viscosity and a good chemical stability. The clearing points are frequently more favourable than those of comparable known liquid crystal components. The compounds with a lateral fluorine on a benzene ring (i.e. with a 2-fluorine-1,4-phenylene group) generally exhibit improved nematic tendencies and slightly modified dielectric anisotropies. The compounds of formula I have a good miscibility with known liquid crystals and can be used basically in any liquid crystals. On the basis of their large positive anisotropy of the dielectric constants they are, however, suitable especially for use in rotation cells and guest-/host cells.

Unless otherwise stated, the term "straight-chain trans-1-alkenyl" as used throughout this application includes the groups vinyl, trans-1-propenyl, trans-1-butenyl, trans-1-pentenyl, trans-1-hexenyl, trans-1-heptenyl, trans-1-octenyl, trans-1-nonenyl, trans-1-decenyl, trans-1-undecenyl and trans-1-dodecenyl.

The term "straight-chain trans-3-alkenyl" includes the groups 3-butenyl, trans-3-pentenyl, trans-3-hexenyl, trans-3-heptenyl, trans-3-octenyl, trans-3-nonenyl, trans-3-decenyl, trans-3-undecenyl and trans-3-dodecenyl.

The term "straight-chain alkyl" includes the groups methyl, ethyl, propyl, butyl, pentyl, hexyl, heptyl, octyl, nonyl, decyl, undecyl and dodecyl.

The term "lateral flourine substituent" as used throughout this specification, unless otherwise stated, refers to a flourine substituent attached to a, 1,4-substituted benzene ring at the 2, 3, 5 or 6 carbon position.

A pyrimidine or m-dioxane ring optionally present in formula I above can be linked in the 2-position or 5-position with the benzene ring. If ring A in formula I above stands for a 2,5-disubstituted pyrimidine ring, then $R^1$ preferably signifies straight-chain alkyl with 1 to 12 carbon atoms or straight-chain trans-3-alkenyl with 4 to 12 carbon atoms. If ring A stands for 1,4-phenylene, then $R^1$ preferably signifies straight-chain trans-3-alkenyl with 4 to 12 carbon atoms. Ring A in formula I above preferably stands for a cyclohexane, pyrimidine or dioxane ring. A lateral fluorine substituent which is optionally present is preferably situated in the ortho-position to the NCS group. Compounds without a fluorine substituent are, however, especially preferred.

In formula I above X preferably stands for a single covalent bond, for 1,4-phenylene or for a 2,5-disubstituted pyrimidine ring. Those compounds in which X represents a single covalent bond are especially preferred.

Preferred residues $R^2$ are straight-chain trans-1-alkenyl with 2 to 7 carbon atoms, straight-chain trans-3-alkenyl with 4 to 7 carbon atoms and straight-chain alkyl with 1 to 7, especially 2 to 5, carbon atoms.

Preferred groups of compounds in accordance with the invention are the compounds of the formulae:

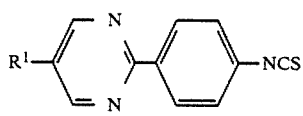

Ia

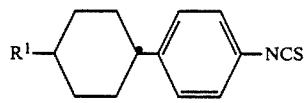

Ib

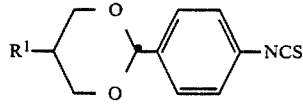

Ic

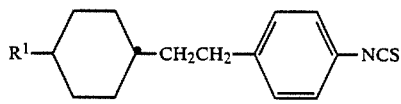

Id

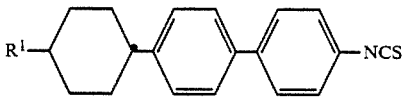

Ie

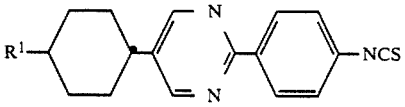

If wherein $R^1$ in each case has the above values.

Especially preferred is the compound of formula Ib wherein $R^1$ is straight-chain trans-1-alkenyl having 2 to 7 carbon atoms or straight-chain trans-3-alkenyl having 4 to 7 carbon atoms.

The compounds of formula I can be manufactured in accordance with the invention by reacting a phenyldithiocarbamate of the formula:

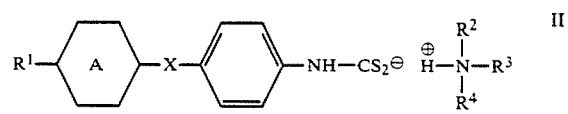

II wherein $R^1$, X and ring A have the above significances, one of the benzene rings optionally has a lateral fluorine substituent, $R^2$ and $R^3$ denote $C_1$–$C_7$-alkyl and $R^4$ signifies hydrogen or $C_1$–$C_7$-alkyl, in the presence of an amine with a chloroformic acid ester.

The reaction of the compounds of formula II can be carried out in a manner known per se. Preferred amines are dialkylamines and especially trialkylamines in which "alkyl" in each case stands for groups with 1 to 7 carbon atoms. Triethylamine is especially preferred. Preferred chloroformic acid esters are the alkyl chloroformates in which the alkyl moiety has 1 to 7 carbon atoms such as methyl chloroformate and ethyl chloroformate. The reaction is conveniently carried out in a polar organic solvent, for example an ether, a chlorinated hydrocarbon or a nitrile such as tetrahydrofuran, dioxan, methylene chloride, chloroform or acetonitrile. The temperature and pressure are not critical. However, the reaction is preferably carried out at atmospheric pressure and a temperature of about 0° to 40° C.

The compounds of formula II are novel. They can be prepared, for example, according to the following Reaction Scheme 1 in which $R^1$, $R^2$, $R^3$, $R^4$, X and ring A have the above significances and in each case one of the benzene rings optionally has a lateral fluorine substituent.

Scheme 1

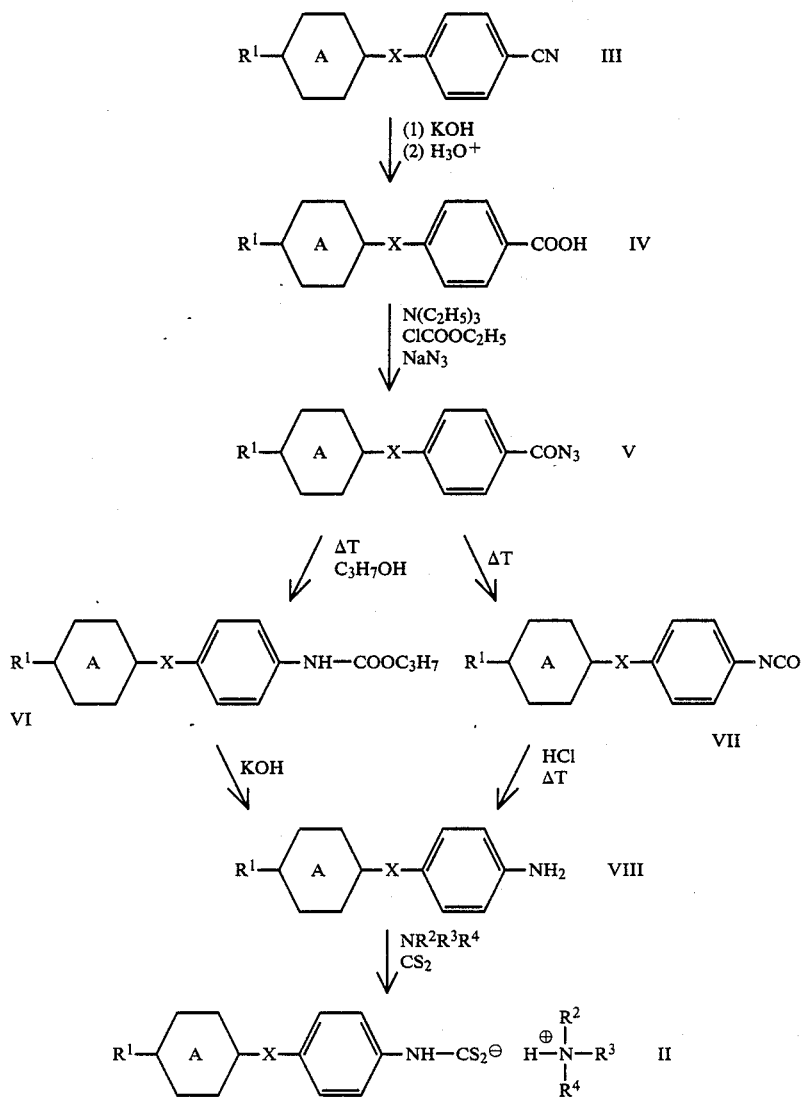

If the compound of formula V contains an alkenyl group or a dioxane ring, then the further reaction is conveniently carried out via the compound of formula VI.

The compounds of formulae III and IV in which $R^1$ signifies straight-chain alkyl are known or are analogues of known compounds.

The compounds of formula III in which $R^1$ signifies straight-chain trans-1-alkenyl or straight-chain trans-3-alkenyl are novel and also have liquid crystalline properties. The preparation of these compounds can be carried out according to methods known per se and is illustrated in more detail on the basis of representative examples in the following Reaction Schemes 2–7 in which $R^5$ signifies hydrogen or straight-chain $C_1$–$C_{10}$-alkyl, $R^6$ signifies straight-chain $C_1$–$C_{10}$-alkyl, $R^7$ signifies straight-chain $C_1$–$C_9$-alkyl, $R^8$ signifies hydrogen or straight-chain $C_1$–$C_8$-alkyl, $R^9$ signifies straight-chain $C_1$–$C_8$-alkyl and Ts signifies p-tosyl.

Scheme 2

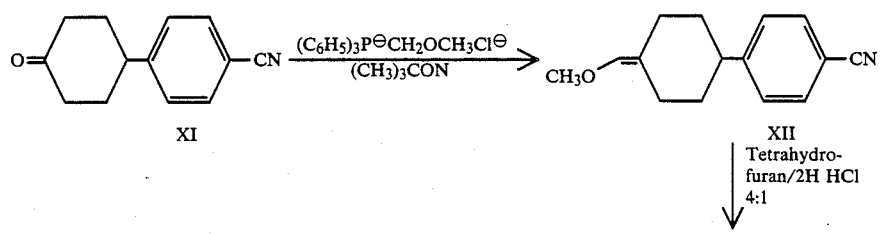

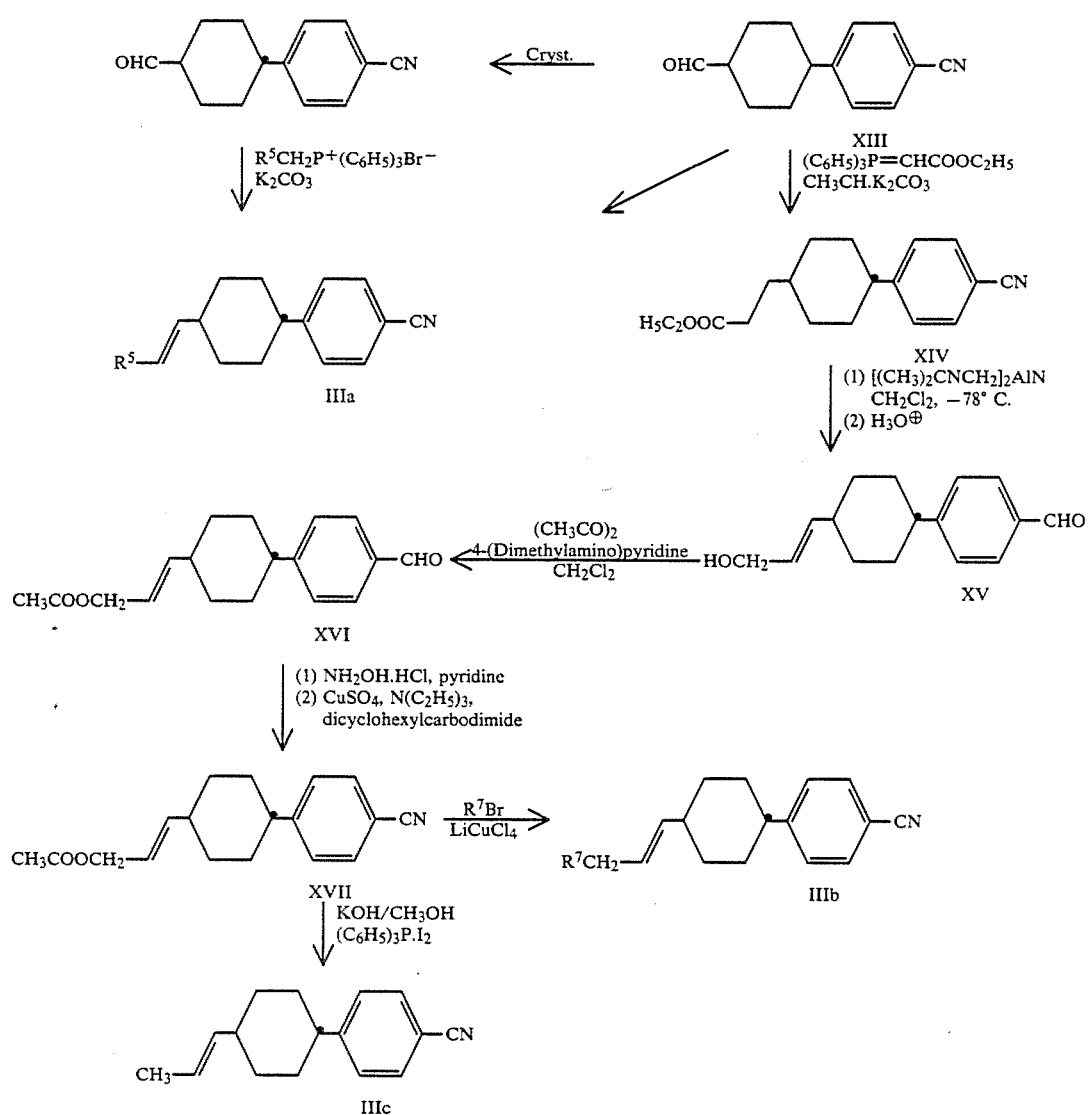
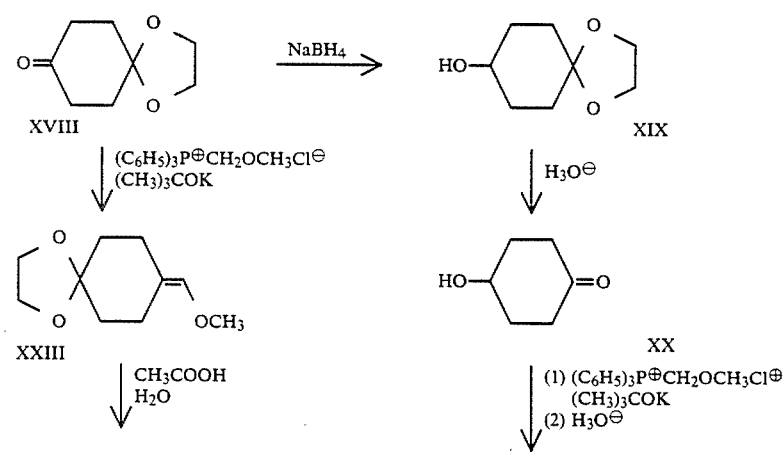

4,915,480
-continued
Scheme 3
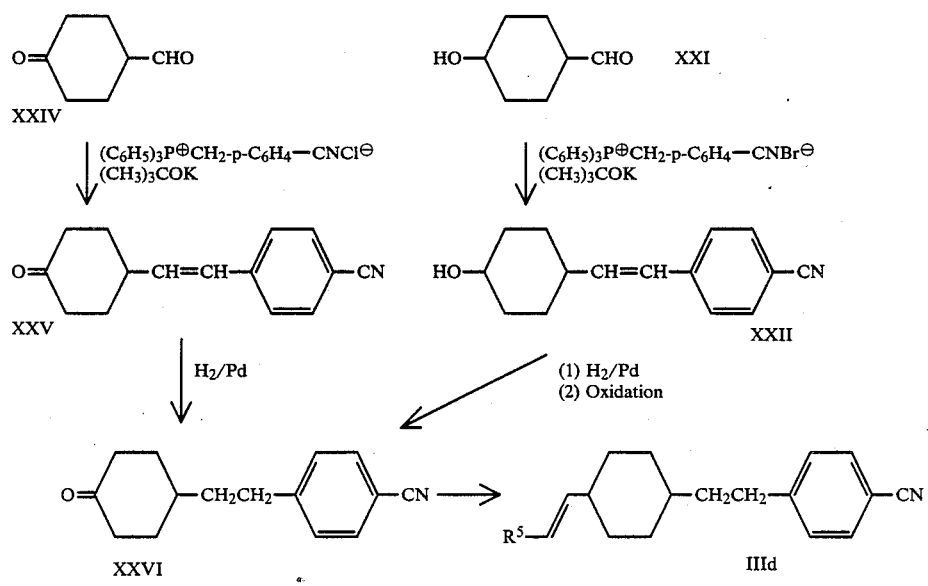
Scheme 4
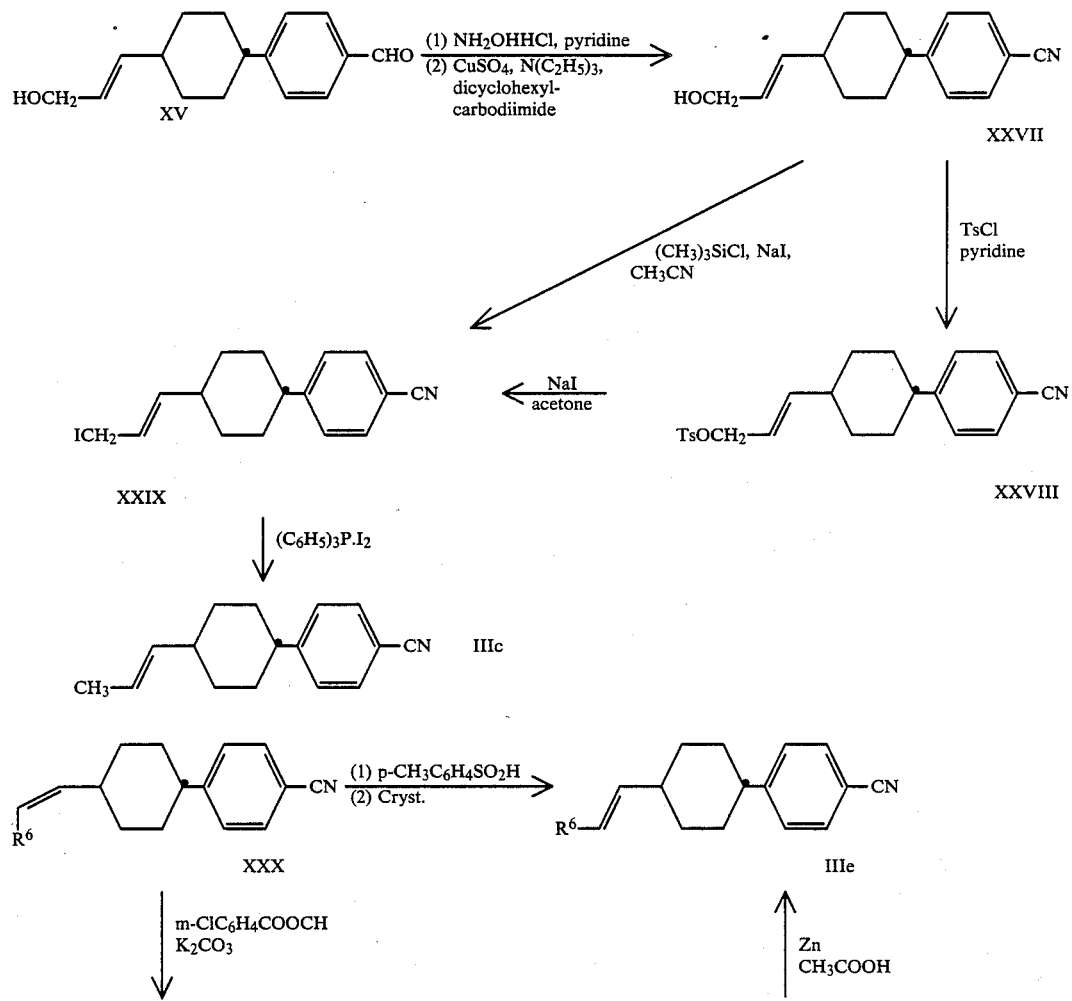

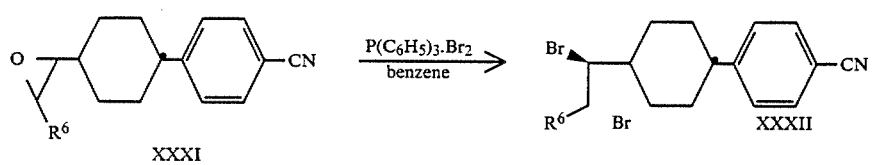
Scheme 4
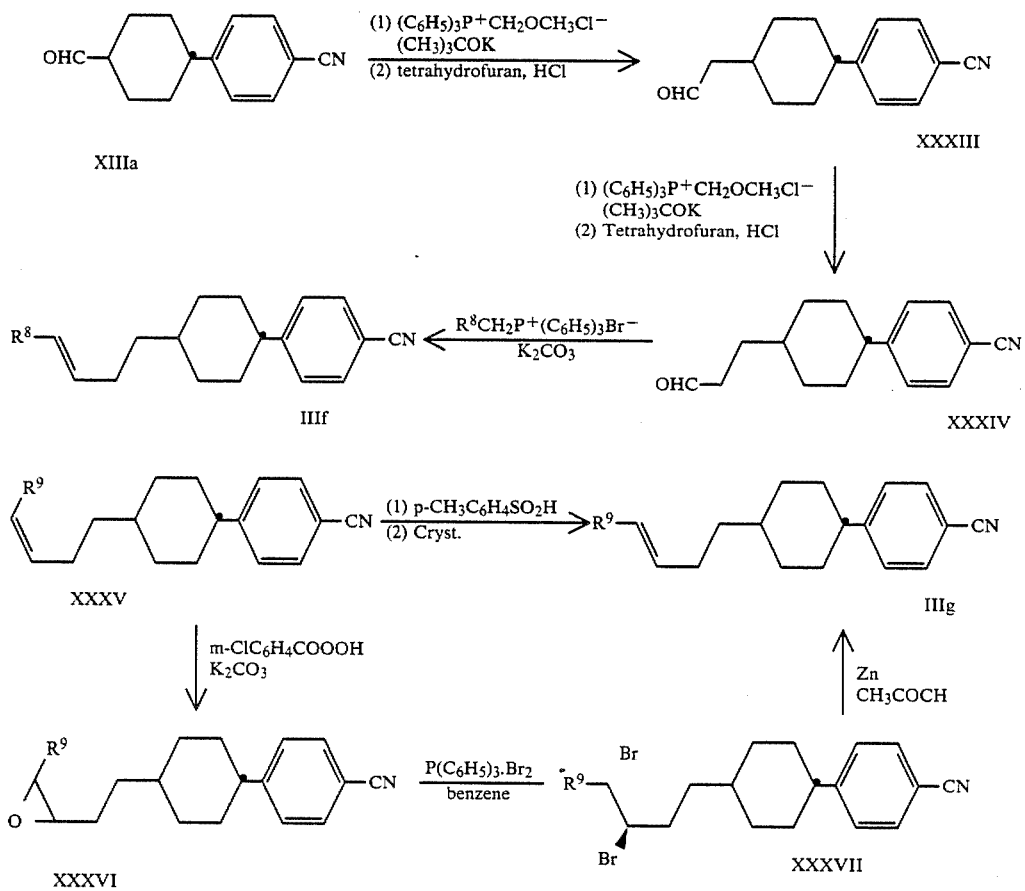
Scheme 5
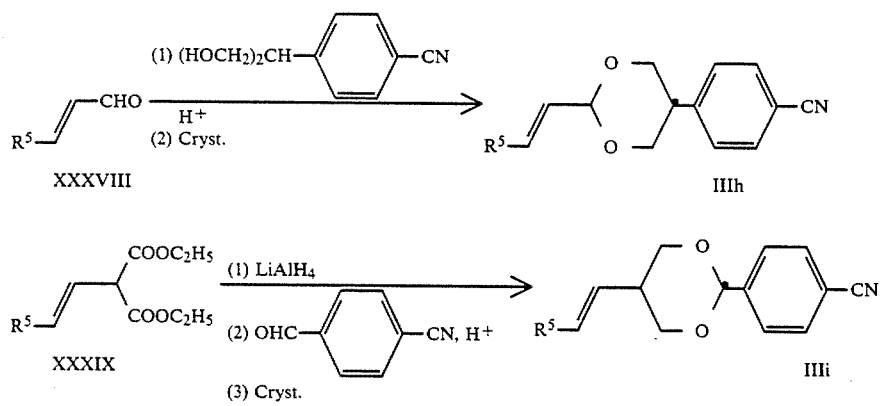
Scheme 6

-continued
Scheme 6
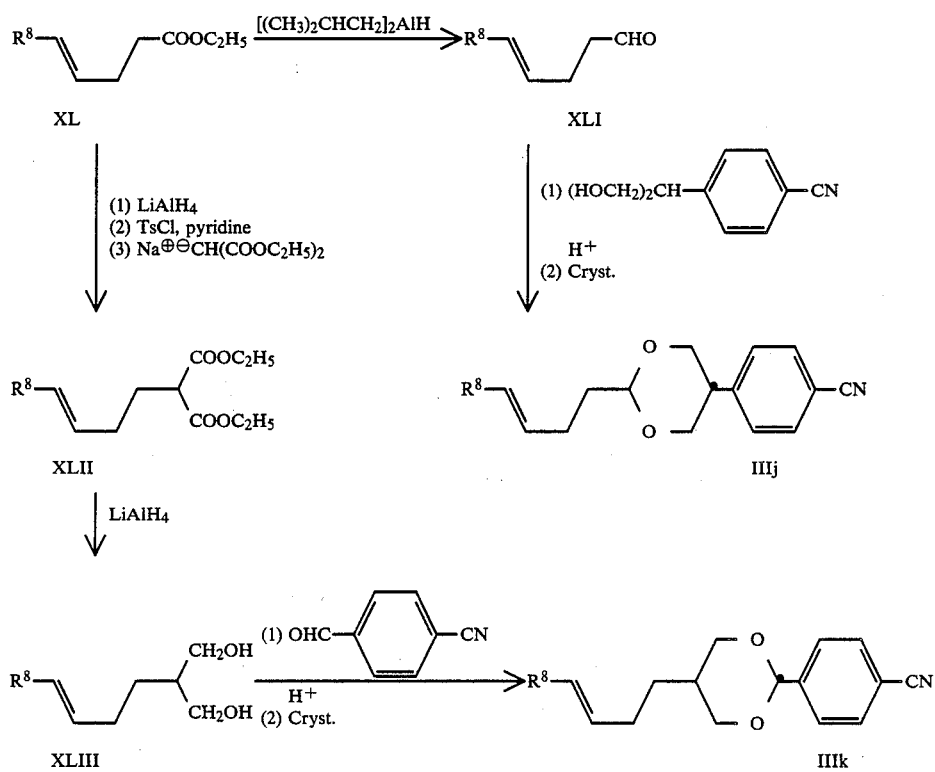
Scheme 7
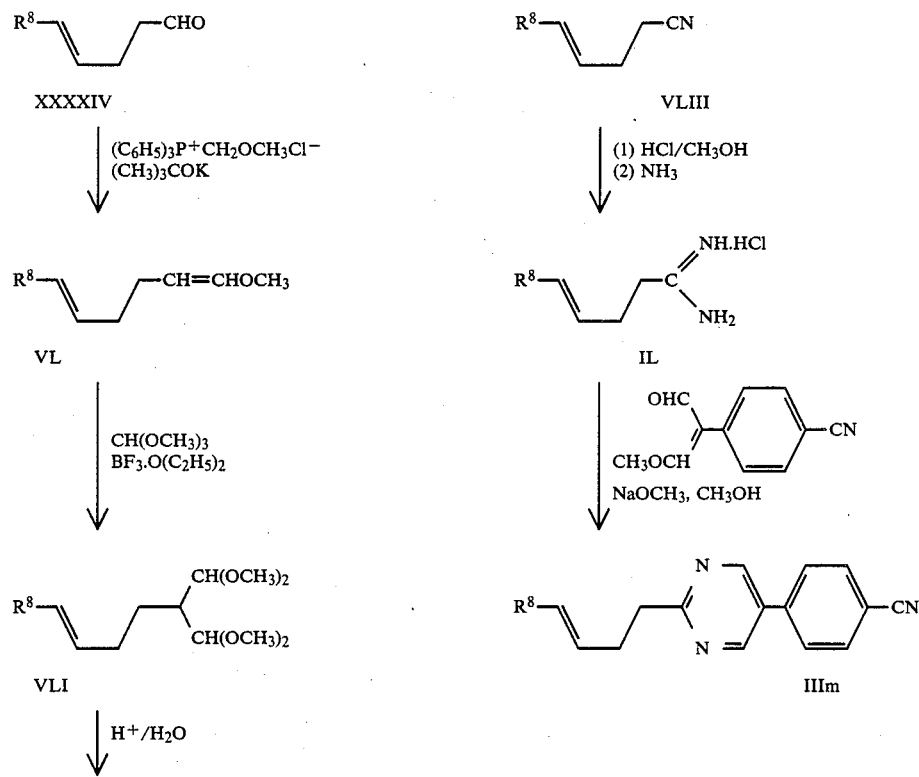

-continued

Scheme 7

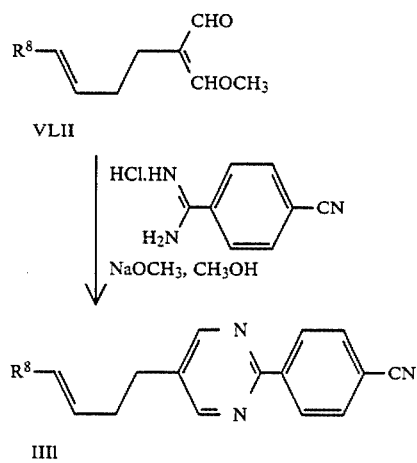

The introduction of other leaving groups in place of the acetoxy group in formula XVII (or analogous compounds) can be carried out according to methods known per se. Examples for an iodide and tosylate are given in Scheme 4. Such compounds can be reduced if desired, e.g. according to the methods described in Chem. Ber. 109, 1586 (1976).

In the preparation of the compounds of formulae IIIa and IIIf in which $R^5$ and $R^8$ signify straight-chain alkyl in accordance with Scheme 2 or 5 there generally results a mixture consisting of cis-alkenyl compound and trans-alkenyl compound. Such mixtures can be separated by chromatography on silica gel coated with silver nitrate. If desired, the cis-alkenyl compounds (or mixture containing predominantly cis-alkenyl compound) can be converted into the corresponding trans-alkenyl compounds in accordance with Scheme 4 or 5.

The reaction of the compound of formula XXVI to give compounds of formula IIId in accordance with Scheme 3 can be carried out in an analogous manner to Scheme 1.

Compounds of formula III which have an alkenyl group and a pyrimidine ring can be prepared according to the methods shown in Scheme 7 or in an analogous manner to Schemes 2, 4 and 5.

The compounds of formula I can be used in the form of mixtures with one another and/or with other liquid crystal components such as e.g. with substances from the classes of Schiff's bases, azobenzenes, azoxybenzenes, phenylbenzoates, cyclohexanecarboxylic acid phenyl esters, cyclohexanecarboxylic acid cyclohexyl esters, biphenyls, terphenyls, phenylcyclohexanes, phenylpyrimidines, diphenylpyrimidines, cyclohexylphenylpyrimidines, phenyldioxanes, 2-cyclohexyl-1-phenylethanes and the like. Such substances are known to the person skilled in the art and many of them are, moreover, commercially obtainable. In particular, the compounds of formula I can also be used in admixture with compounds of formula III above.

On the basis of the favourable properties of the compounds of formula I and their good miscibility with other liquid crystal components the amount of the compounds of formula I in the mixtures in accordance with the invention can vary in wide limits. The mixtures in accordance with the invention preferably contain about 1–60 wt.%, particularly about 5–40 wt.%, of compounds of formula I.

Preferred components which can be used in admixture with one or more compounds of formula I are the compounds of the formulae:

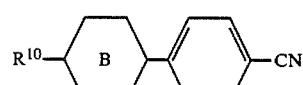  L

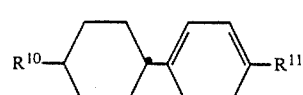  LI

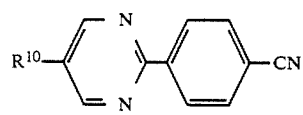  LII

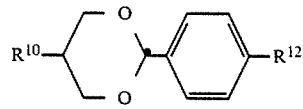  LIII

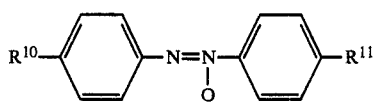 LIV

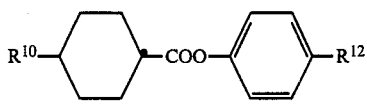 LV

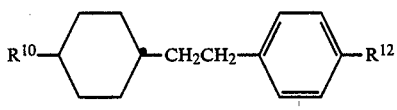 LVI

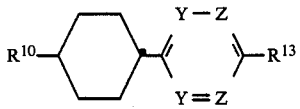 LVII

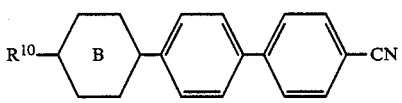 LVIII

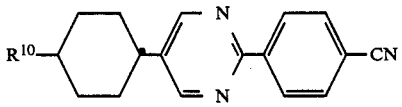 LIX

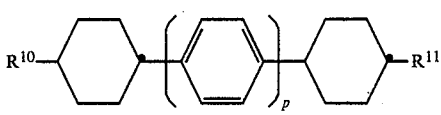 LX

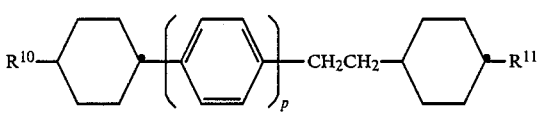 LXI

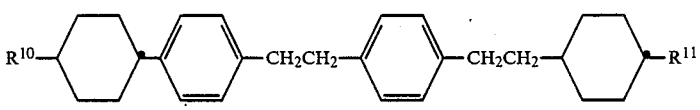 LXII wherein ring B represents 1,4-phenylene or trans-1,4-cyclohexylene, one of the symbols Y and Z stands for N and the other stands for CH, $R^{10}$ and $R^{11}$ denote straight-chain $C_1$-$C_7$-alkyl, $R^{12}$ signifies cyano or straight-chain $C_1$-$C_6$-alkoxy, $R^{13}$ denotes straight-chain $C_1$-$C_7$-alkyl, p-($C_1$-$C_7$-alkyl)phenyl or trans-4-($C_1$-$C_7$-alkyl)cyclohexyl and p stands for 0 or 1, and the compounds of the above formulae IIIa, IIIf, IIIi, IIIk and IIIl (Schemes 2 and 5–7).

Further, the mixtures in accordance with the invention can contain suitable, optically active compounds, for example optically active biphenyls, and/or dichroic colouring substances, for example azo, azoxy or anthraquinone colouring substances. The amount of such compounds is determined by the solubility and the desired pitch, colour, extinction and the like. Preferably, the amount of optically active compounds amounts to a maximum of about 4 wt.% and the amount of dichroic colouring substances amounts to a maximum of about 10 wt.%.

The manufacture of the liquid crystalline mixtures in accordance with the invention can be carried out in a manner known per se, e.g. by heating a mixture of the components to a temperature barely above the clearing point and subsequently cooling down.

The manufacture of electro-optical devices which contain a mixture in accordance with the invention as the dielectric can also be carried out in a manner known per se, e.g. by evacuating a suitable cell and introducing the mixture into the evacuated cell.

The following Mixtures Nos. 1–5 are examples of preferred mixtures in accordance with the invention. $V_{10}$ and $V_{50}$ denote the voltage for 10% or 50% transmission, $p_o = (V_{50}-V_{10})/V_{10}$ is a measure for the steepness of the transmission curve, $t_{on}$ and $t_{off}$ denote the switching-on time or the switching-off time (in a rotation cell at 2.5 $V_{10}$ and angle of tilt 0°) and $k_{11}$ (splay) and $k_{33}$ (bend) are elastic constants. Unless otherwise indicated, the measurements were carried out as written at 22° C.

Mixture 1
11.2 wt.% of p-(5-butyl-2-pyrimidinyl)benzonitrile,
3.4 wt.% of p-(5-pentyl-2-pyrimidinyl)benzonitrile,
6.6 wt.% of p-(5-heptyl-2-pyrimidinyl)benzonitrile, 13.35 wt.% of trans-4-butylcyclohexanecarboxylic acid p-ethoxyphenyl ester,
17.55 wt.% of trans-4-butylcyclohexanecarboxylic acid p-pentyloxyphenyl ester,
12.3 wt.% of trans-4-pentylcyclohexanecarboxylic acid p-methoxyphenyl ester,
19.05 wt.% of trans-4-pentylcyclohexanecarboxylic acid p-propyloxyphenyl ester,
7.85 wt.% of p-[5-(trans-4-ethylcyclohexyl)-2-pyrimidinyl]-benzonitrile,
8.7 wt.% of p-[trans-4-(trans-1-propenyl)cyclohexyl]phenyl isothiocyanate;
m.p. less than $-25°$ C., cl.p. $62°$ C., nematic; $V_{10}=1.521$ V, $p_o=0.121$; $k_{33}/k_{11}=0.98$.

Mixture 2
6.5 wt.% of p-(trans-4-propylcyclohexyl)benzonitrile,
12.3 wt.% of p-[trans-4-(3-butenyl)cyclohexyl]benzonitrile,
7.3 wt.% of p-[trans-4-(trans-3-pentenyl)cyclohexyl]benzonitrile,
6.0 wt.% of 1-ethyl-4-(trans-4-propylcyclohexyl)benzene,
18.0 wt.% of 1-ethoxy-4-[2-(trans-4-propylcyclohexyl)ethyl]benzene,
4.7 wt.% of 4-cyano-4'-(trans-4-pentylcyclohexyl)biphenyl,
3.6 wt.% of 4-cyano-4'-[trans-4-(3-butenyl)cyclohexyl]biphenyl,
14.7 wt.% of 1-[2-(trans-4-butylcyclohexyl)ethyl]-4-(trans-4-pentylcyclohexyl)benzene,
5.0 wt.% of 4-[2-(trans-4-butylcyclohexyl)ethyl]-4'-(trans-4-pentylcyclohexyl)biphenyl,
8.0 wt.% of 4-[2-(trans-4-butylcyclohexyl)ethyl]-4'-(trans-4-pentylcyclohexyl)-1,1'-ethylenedibenzene,
13.9 wt.% of p-[trans-4-(trans-3-pentenyl)cyclohexyl]phenyl isothiocyanate;
m.p. less than $-25°$ C., cl.p. $85°$ C., nematic; $V_{10}=2.51$ V, $P_o=0.127$; $t_{on}=31$ ms, $t_{off}=36$ ms.

Mixture 3
13.50 wt.% of p-[trans-4-(trans-1-butenyl)cyclohexyl]benzonitrile,
9.87 wt.% of p-[trans-4-(3-butenyl)cyclohexyl]benzonitrile,
7.00 wt.% of 1-ethyl-4-(trans-4-propylcyclohexyl)benzene,
8.00 wt.% of 1-ethoxy-4-(trans-4-propylcyclohexyl)benzene,
5.00 wt.% of 1-ethyl-4-[2-(trans-4-propylcyclohexyl)ethyl]benzene,
3.59 wt.% of 4-cyano-4'-(trans-4-pentylcyclohexyl)biphenyl,
2.74 wt.% of 4-cyano-4'-[trans-4-(3-butenyl)cyclohexyl]biphenyl,
7.00 wt.% of 4-propyl-4'-[trans-4-(trans-3-pentenyl)cyclohexyl]biphenyl,
8.17 wt.% of p-[trans-4-(trans-3-pentenyl)cyclohexyl]benzoic acid p'-propylphenyl ester,
11.19 wt.% of 1-[2-(trans-4-butylcyclohexyl)ethyl]-4-(trans-4-pentylcyclohexyl)benzene,
5.00 wt.% of 4-[2-(trans-4-butylcyclohexyl)ethyl]-4'-(trans-4-pentylcyclohexyl)biphenyl,
6.00 wt.% of 4-[2-(trans-4-butylcyclohexyl)ethyl]-4'-(trans-4-pentylcyclohexyl)-1,1'-ethylenedibenzene,
12.94 wt.% of p-[trans-4-(trans-3-hexenyl)cyclohexyl]phenyl isothiocyanate;
m.p. less than $-30°$ C., cl.p. $92°$ C., nematic; $V_{10}=2.32$ V, $p_o=0.125$; $t_{on}=30$ ms, $t_{off}=40$ ms.

Mixture 4
13 wt.% of p-(5-butyl-2-pyrimidinyl)benzonitrile,
4 wt.% of p-(5-pentyl-2-pyrimidinyl)benzonitrile,
7 wt.% of p-(5-heptyl-2-pyrimidinyl)benzonitrile,
11 wt.% of trans-4-butylcyclohexanecarboxylic acid p-ethoxyphenyl ester,
12 wt.% of trans-4-butylcyclohexanecarboxylic acid p-pentyloxyphenyl ester
10 wt.% of trans-4-pentylcyclohexanecarboxylic acid p-methoxyphenyl ester,
16 wt.% of trans-4-pentylcyclohexanecarboxylic acid p-propyloxyphenyl ester,
7 wt.% of p-[5-(trans-4-ethylcyclohexyl)-2-pyrimidinyl]benzonitrile,
20 wt.% of p-(5-pentyl-2-pyrimidinyl)phenyl isothiocyanate;
m.p. less than $-20°$ C., cl.p. $59°$ C., nematic; $V_{10}=1.474$ V, $p_o=0.115$.

Mixture 5
10.27 wt.% of p-(5-butyl-2-pyrimidinyl)benzonitrile,
3.16 wt.% of p-(5-pentyl-2-pyrimidinyl)benzonitrile,
5.53 wt.% of p-(5-heptyl-2-pyrimidinyl)benzonitrile,
8.69 wt.% of trans-4-butylcyclohexanecarboxylic acid p-ethoxyphenyl ester,
9.48 wt.% of trans-4-butylcyclohexanecarboxylic acid p-pentyloxyphenyl ester,
7.90 wt.% of trans-4-pentylcyclohexanecarboxylic acid p-methoxyphenyl ester,
12.64 wt.% of trans-4-pentylcyclohexanecarboxylic acid p-propyloxyphenyl ester,
10.00 wt.% of 1-ethyl-4-[2-(trans-4-propylcyclohexyl)ethyl]benzene,
7.00 wt.% of 5-(trans-4-ethylcyclohexyl)-2-(p-pentylphenyl)-pyrimidine,
4.00 wt.% of 5-(p-butylphenyl)-2-(p-pentylphenyl)-pyrimidine,
5.53 wt.% of p-[5-(trans-4-ethylcyclohexyl)-2-pyrimidinyl]benzonitrile,
15.80 wt.% of p-(5-pentyl-2-pyrimidinyl)phenyl isothiocyanate;
m.p. less than $-20°$ C., cl.p. $59°$ C., menatic; $V_{10}=1.692$ V, $p_o=0.114$; $k_{33}/k_{11}=0.76$.

The following Examples 1 through 12 illustrate the manufacture of the compounds of formula I and of the novel compounds of formula III of the invention. Unless otherwise stated, percentages and ratios relating to solvent mixtures are expressed in volume, purity data determined by gas chromatography are expressed in area %, and the remaining percentages and ratios are expressed in weight. Temperatures are in degrees Celsius (°C.), normal pressure is about 1 atmosphere, and room temperature is about $23°$ C. C signifies a crystalline phase, S signifies a smectic phase, $S_B$ signifies a smetic B phase, N signifies a nematic phase and I signifies the isotropic phase. Unless indicated otherwise, the Examples were carried out as written.

EXAMPLE 1

6.77 g of triethylammonium p-(5-butyl-2-pyrimidinyl)phenyldithiocarbamate were largely dissolved in 60 ml of chloroform and 2.5 ml of triethylamine. The mixture was subsequently treated dropwise with 2.00 ml of methyl chloroformate within 5 minutes while stirring and cooling with an ice bath. The ice bath was removed after 10 minutes. After a further 60 minutes the yellowish solution was washed once with 20 ml of 0.5N hydrochloric acid and three times with 20 ml of water each time, dried over sodium sulphate and concentrated. Chromatography of the residue on 60 g of silica gel with hexane/ethyl acetate (vol. 95:5) gave 3.65 g of p-(5-butyl-2-pyrimidinyl)phenyl isothiocyanate which was recrystallized twice from hexane for further purification. Yield 3.17 g; m.p. (C—S) 60.8° C., cl.p. (S—I) 77.8° C.

The triethylammonium p-(5-butyl-2-pyrimidinyl)-phenyldithiocarbamate used as the starting material was prepared as follows:

(a) A suspension of 12.62 g of p-(5-butyl-2-pyrimidinyl)benzoic acid in 150 ml of acetone was treated dropwise with a solution of 8.1 ml of triethylamine in 25 ml of acetone while cooling with an ice-/sodium chloride bath (internal temperature −4° C.) and thereafter dropwise within 15 minutes with a solution of 4.9 ml of methyl chloroformate in 25 ml of acetone. The suspension was stirred for a further 75 minutes and then treated dropwise within 10 minutes with a solution of 4.90 g of sodium azide in 17.5 ml of water. The mixture was stirred for another 1 hour while cooling with the ice/sodium chloride bath and then for 30 minutes without cooling. The mixture was poured on to 300 ml of ice-water and extracted once with 250 ml of diethyl ether and twice with 100 ml of diethyl ether each time. The extracts were washed with 100 ml of water, dried and concentrated in vacuo at a bath temperature of 35° C., whereby 13.32 g of solid, yellowish p-(5-butyl-2-pyrimidinyl)benzoic acid azide were obtained. The azide was dissolved in 100 ml of toluene and the solution was added dropwise slowly to a flask heated to 90° C., whereby a strong evolution of nitrogen took place. The solution was heated to 108° C. for a further 1.5 hours and then concentrated. There were obtained 11.59 g of crude, pale yellow p-(5-butyl-2-pyrimidinyl)-phenyl isocyanate; m.p. 48° C.

(b) 8.11 g of crude p-(5-butyl-2-pyrimidinyl)phenyl isocyanate were introduced in small portions into 40 ml of 8N hydrochloric acid heated to 60° C., whereby strong foaming took place. After completion of the addition the mixture was heated to slight boiling for 4 hours and then poured on to ice and an excess of solid sodium carbonate. The aqueous phase was extracted once with 300 ml of diethyl ether and twice with 100 ml of diethyl ether each time. The combined extracts were filtered. The filtrate was washed twice with water, dried over sodium sulphate and concentrated, whereby 5.16 g of yellowish, crystalline p-(5-butyl-2-pyrimidinyl)aniline were obtained; m.p. 154.5°–155.5° C.

(c) A solution of 5.10 g of p-(5-butyl-2-pyrimidinyl)aniline in 30 ml of dioxan, 1.70 ml of carbon disulphide and 3.44 ml of triethylamine was placed in a refrigerator (0° C.) for 90 hours. The yellow precipitate obtained was filtered off, washed with diethyl ether and dried. 6.77 g of triethylammonium p-(5-butyl-2-pyrimidinyl)-phenyldithiocarbamate were obtained which was processed without additional purification.

The following compounds were manufactured in an analogous manner:

p-(5-Pentyl-2-pyrimidinyl)phenyl isothiocyanate; m.p. (C—S) 46° C., cl.p. (S—I) 85.5° C., p-[5-(trans-4-ethylcyclohexyl)-2-pyrimidinyl-phenyl isothiocyanate; m.p. (C—S) 114.0° C., phase transition S—N 159.5° C., cl.p. (N—I) 228.5° C., p-(2-pentyl-5-pyrimidinyl)phenyl isothiocyanate; m.p. (C—I) 92° C., cl.p. (N—I) 43.5° C.

EXAMPLE 2

428 mg of triethylammonium p-[trans-4-(trans-1-pentenyl)cyclohexyl]phenyldithiocarbamate were dissolved in 4 ml of chloroform and the solution was treated under argon with 284 μl of triethylamine. The mixture was subsequently cooled to 0° C. and treated dropwide with 194 μl of ethyl chloroformate. The mixture was stirred at 0° C. for a further 10 minutes and then at room temperature for 1 hour. The reaction mixture was subsequently partitioned between 100 ml of diethyl ether and 100 ml of water. The aqueous phase was back-extracted twice with 100 ml of diethyl ether each time. The organic phases were washed twice with 100 ml of water each time, dried over magnesium sulphate and concentrated. Low-pressure chromatography (0.5 bar) of the oily residue (450 mg) on 35 g of silica gel with ethyl acetate/petroleum ether (vol. 7:93) gave 234 mg (51%) of p-[trans-4-(trans-1-pentenyl)cyclohexyl]phenyl isothiocyanate as colourless crystals. By recrystallization from 10 ml of methanol at 0° C. there were obtained 119 mg of p-[trans-4-(trans-1-pentenyl)cyclohexyl]phenyl isothiocyanate of melting point (C—I) 61.2° C. and cl.p. (N—I) 49.0° C.

The triethylammonium p-[trans-4-(trans-1-pentenyl)-cyclohexyl]phenyldithiocarbamate used as the starting material was prepared as follows:

(a) A mixture of 100 mg of p-[trans-4-(trans-1-pentenyl)cyclohexyl]benzonitrile and 10 ml of a 10% solution of potassium hydroxide in diethylene glycol was boiled at 180° C. for 1 hour while gassing with argon in a round flask provided with a magnetic stirrer and a reflux condenser. After cooling the brown reaction mixture was made acid with 25% hydrochloric acid and partitioned between 70 ml of dichloromethane and 70 ml of water. The aqueous phase was back-extracted three times with 70 ml of dichloromethane each time. The organic phases were washed twice with 70 ml of water each time and dried over magnesium sulphate and active carbon. After separating the solvent in a rotary evaporator there were obtained 99 mg (92%) of p-[trans-4-(trans-1-pentenyl)cyclohexyl]benzoic acid as white, intensively smelling crystals; Rf-value 0.44 (ethyl acetate/petroleum ether, vol. 3:7).

(b) A suspension of 558 mg of p-[trans-4-(trans-1-pentenyl)cyclohexyl]benzoic acid in 20 ml of acetone and 1 ml of water was cooled to 0° C. and treated slowly with a solution of 571 μl of triethylamine in 4 ml of acetone, whereby a clear solution formed. The mixture was subsequently treated dropwise with a solution of 487.9 μl of ethyl chloroformate in 2 ml of acetone, whereby a white flocculent precipitate separated. The mixture was stirred at 0° C. for a further 30 minutes, then treated dropwise with a solution of 366.2 mg of sodium azide in 2 ml of water and stirred at 0° C. for a further 1 hour. The reaction mixture was thereafter partitioned between 150 ml of diethyl ether and 150 ml of water. The aqueous phase was back-extracted twice with 150 ml of diethyl ether each time. The organic phases were washed twice with 100 ml of water each time, dried over magnesium sulphate and concentrated. Low-pressure chromatography (0.5 bar) of the greenish, liquid crystalline residue (590 mg) on 70 g of silica gel with ethyl acetate/petroleum ether (vol. 1:9) gave 539 mg (89%) of p-[trans-4-(trans-1-pentenyl)cyclohexyl]benzoic acid azide as colourless crystals; Rf-value 0.53 (ethyl acetate/petroleum ether, vol. 1:9).

(c) A mixture of 539 mg of p-[trans-4-(trans-1-pentenyl)cyclohexyl]benzoic acid azide and 10 ml of propanol was boiled at reflux for 2.5 hours while gassing with argon and thereafter concentrated. Low-pressure chromatography (0.5 bar) of the white, crystalline residue on 70 g of silica gel with ethyl acetate/petroleum ether (vol. 1:9) gave 515 mg (86%) of propyl p-[trans-4-(trans-1-pentenyl)cyclohexyl]phenylcarbamate as colourless crystals; Rf-value 0.33 (ethyl acetate/petroleum ether, vol. 1:9).

(d) A mixture of 118 mg of propyl p-[trans-4-(trans-1-pentenyl)cyclohexyl]phenylcarbamate and 12.5 ml of a 10% solution of potassium hydroxide in diethylene glycol/water (vol. 4:1) was boiled at 120° C. for 1 hour, then cooled to room temperature and partitioned between 70 ml of diethyl ether and 70 ml of water. The aqueous phase was back-extracted twice with 70 ml of diethyl ether each time. The organic phases were washed twice with 50 ml of water each time, dried over magnesium sulphate and concentrated. Low-pressure chromatography (0.5 bar) of the brown, crystalline residue (150 mg) on 35 g of silica gel with ethyl acetate/petroleum ether (vol. 15:85) gave 76.6 mg (88%) of p-[trans-4-(trans-1-pentenyl)cyclohexyl]aniline as slightly yellowish crystals; purity 97%; Rf-value 0.24 (ethyl acetate/petroleum ether, vol. 1:5).

(e) A solution of 390 mg of p-[trans-4-(trans-1-pentenyl)cyclohexyl]aniline (purity 93%) in 4 ml of hexane was treated successively with 446 μl of triethylamine and 214 μl of carbon disulphide and the mixture was then left to stand at 0° C. for 65 hours. The yellow precipitate obtained was filtered off, washed twice with hexane and dried in a high vacuum. There were obtained 428 mg of triethylammonium p-[trans-4-(trans-1-pentenyl)cyclohexyl]phenyldithiocarbamate which was processed directly without additional purification.

The following compounds were manufactured in an analogous manner:

p-[Trans-4-(trans-1-propenyl)cyclohexyl]phenyl isothiocyanate; m.p. (C—I) 88.5° C., virtual cl.p. 47° C., p-[trans-4-(trans-3-pentenyl)cyclohexyl]phenyl isothiocyanate; m.p. (C—N) 59.2° C., cl.p. (N—I) 65.2° C., p-[trans-4-(trans-1-butenyl)cyclohexyl]phenyl isothiocyanate; m.p. (C—I) 48.2° C., cl.p. (N—I) 35.6° C., p-[trans-4-(trans-1-hexenyl)cyclohexyl]phenyl isothiocyanate; m.p. (C—N 16.3° C., cl.p. (N—I) 23.5° C., p-[trans-4-(3-butenyl)cyclohexyl]phenyl isothiocyanate; m.p. (C—N) 24.6° C., cl.p. (N—I) 43.7° C., p-[trans-4-(trans-3-hexenyl)cyclohexyl]phenyl isothiocyanate; m.p. (C—N) 24.4° C., cl.p. (N—I) 37.2° C., 4'-(3-butenyl)-4-biphenylyl isothiocyanate;

4'-(trans-3-pentenyl)-4-biphenylyl isothiocyanate;

p-[2-(trans-4-propylcyclohexyl)ethyl]phenyl isothiocyanate; m.p. (C—I) 43.0° C., cl.p. (N—I) 38.6° C., p-[2-(trans-4-butylcyclohexyl)ethyl]phenyl isothiocyanate; m.p. (C—N) 23.5° C., cl.p. (N—I) 33.6° C., p-[2-(trans-4-pentylcyclohexyl)ethyl]phenyl isothiocyanate; m.p. (C—N) 41.0° C., cl.p. (N—I) 47.5° C., p-[2-(trans-4-hexylcyclohexyl)ethyl]phenyl isothiocyanate; m.p. (C—I) 50.0° C., cl.p. (N—I) 41.4° C., p-[2-(trans-4-heptylcyclohexyl)ethyl]phenyl isothiocyanate; m.p. (C—I)) 56.2° C., cl.p. (N—I) 49.2° C., 4'-(trans-4-ethylcyclohexyl)-4-biphenylyl isothiocyanate; m.p. (C—N) 151.0° C. cl.p. (N—I) 214.5° C., 4'-(trans-4-propylcyclohexyl)-4-biphenylyl isothiocyanate; m.p. (C—N) 149.3° C., cl.p. (N—I) 240.5° C., 4'-(trans-4-butylcyclohexyl)-4-biphenylyl isothiocyanate; m.p. (C—S) 119.8° C., phase transition S—N 132.5° C., cl.p. (N—I) 233.0° C., 4'-(trans-4-pentylcyclohexyl)-4-biphenylyl isothiocyanate; m.p. (C—S) 123.0° C., phase transition S—N 133.0° C., cl.p. (N—I) 233.5° C., 4'-(trans-4-hexylcyclohexyl)-4-biphenylyl isothiocyanate; m.p. (C—S) 96.2° C., phase transition S—N 147.0° C., cl.p. (N—I) 223.0° C., 4'-(trans-4-heptylcyclohexyl)-4-biphenylyl isothiocyanate; m.p. (C—S) 108.8° C., phase transition S—N 156.0° C., cl.p. (N—I) 219.5° C.

EXAMPLE 3

A solution of 7.1 mmol of ethylmagnesium bromide (prepared from 172 mg of magnesium and 530 μl of ethyl bromide) in 20 ml of absolute tetrahydrofuran was placed at −78° C. while gassing with argon in a sulphonation flask provided with a thermometer, a dropping funnel and a serum cap and treated successively with 3.6 ml of a 0.48M solution of dilithium tetrachlorocuprate in absolute tetrahydrofuran and with a solution of 500 mg of p-[trans-4-(3-acetoxy-trans-1-propenyl)cyclohexyl]benzonitrile in 10 ml of absolute tetrahydrofuran. After completion of the addition, the reaction mixture was warmed to −15° C., stirred at this temperature for 1.5 hours, subsequently treated with 20 ml of saturated ammonium chloride solution and stirred at room temperature for a further 1 hour. The aqueous phase, which was now deep blue, was separated and extracted twice with 50 ml of diethyl ether each time. The organic phases were washed twice with 50 ml of water each time, dried over magnesium sulphate and concentrated. Low-pressure chromatography (0.5 bar) of the residue (0.4 g) on silica gel with ethyl acetate/petroleum ether (vol. 3.97) gave 375 mg of crude p-[trans-4-(trans-1-pentenyl)cyclohexyl]benzonitrile which, according to analysis by gas chromatography, was contaminated to 8.5% with p-[trans-4-(trans-1-pentenyl)cyclohexyl]propiophenone and to 4.0% with p-[trans-4-(1-vinylpropyl)cyclohexyl]benzonitrile. Treatment of this crude product with an excess of sodium borohydride in methanol at 0° C. (in order to reduce the propiophenone), working-up, low-pressure chromatography (0.5 bar) on silica gel with ethyl acetate/petroleum ether (vol. 1:9) and finally recrystallization from methanol at −78° C. gave p-[trans-4-(trans-1-pentenyl)-cyclohexyl]benzonitrile in a purity of 98.6%; m.p. (C—N) 15.5° C., cl.p. (N—I) 57.0° C.

The p-[trans-4-(3-acetoxy-trans-1-propenyl)cyclohexyl]benzonitrile used as the starting material was prepared as follows:

(a) 10.4 g of triphenyl-methoxymethyl-phosphonium chloride were suspended in 60 ml of t-butyl methyl ether while gassing with argon in a sulphonation flask provided with a thermometer, a mechanical stirrer, a dropping funnel and a solid substance addition tube and treated at −10° C. within 10 minutes with 3.6 g of solid potassium t-butylate. After completion of the addition, the mixture was stirred at −10° C. to 0° C. for a further 30 minutes and then the deep orange, heterogeneous reaction mixture was treated dropwise at 0° C. with a solution of 4.2 g of 4-(p-cyanophenyl)cyclohexanone in 50 ml of absolute tetrahydrofuran. The reaction mixture was subsequently stirred at room temperature for a further 2 hours, then poured into 500 ml of hexane and filtered. Low-pressure chromatography (0.5 bar) of the concentrated residue (7.1 g) on silica gel with ethyl acetate/petroleum ether (vol. 5:95) gave 4.5 g (94%) of p-[4-(methoxymethylene)cyclohexyl]benzonitrile as a colourless oil; purity 95%, Rf-value (ethyl acetate/petroleum ether, vol. 1:9) 0.30.

(b) A mixture of 4.2 g of p-[4-(methoxymethylene)cyclohexyl]benzonitrile and 100 ml of tetrahydrofuran/2N hydrochloric acid (vol. 4:1) was heated to reflux for 30 minutes in a round flask. The mixture was subsequently poured into 100 ml of water and extracted three times with 100 ml of diethyl ether each time. The organic phases were washed once with 100 ml of water, dried over magnesium sulphate and concentrated. There were obtained 3.9 g (100%) of 4-(p-cyanophenyl)cyclohexanecarboxaldehyde as a colourless oil which was used in the next step without further purification: trans/cis ratio about 3:1, Rf-value (ethyl acetate/petroleum ether, vol. 3:7) 0.41. By recrystallization from hexane there could be obtained pure trans-4-(p-cyanophenyl)cyclohexanecarboxaldehyde; m.p. 57.1° C.

(c) A mixture of 3.9 g of the 4-(p-cyanophenyl)cyclohexanecarboxaldehyde obtained above and 272 mg of powdered potassium carbonate in 60 ml of ethanol was placed at room temperature while gassing with argon in a sulphonation flask provided with a solid substance addition tube and treated within 15 minutes with 7.6 g of solid ethoxycarbonylmethylene-triphenylphosphorane. The reaction mixture was subsequently stirred at room temperature for 2 hours, then freed from ethanol on a rotary evaporator, the residue was taken up in 100 ml of water and extracted three times with 100 ml of methylene chloride each time. The organic phases were washed twice with 100 ml of water each time, dried over magnesium sulphate and concentrated. Low-pressure chromatography (0.5 bar) of the residue (12 g) on silica gel with toluene/petroleum ether/ethyl acetate (vol. 5:4:1) gave 5.2 g of a crystalline mass which, after crystallization from 500 ml of hexane, yielded 3.9 g (75%) of ethyl trans-3-[trans-4-(p-cyanophenyl)cyclohexyl]acrylate as colourless crystals of melting point 125° C.

(d) A solution of 1.0 g of ethyl trans-3-[trans-4-(p-cyanophenyl)cyclohexyl]acrylate in 25 ml of methylene chloride was placed at −78° C. while gassing with argon in a sulphonation flask provided with a thermometer and a serum cap and treated within 10 minutes with 15.0 ml of a 0.84M solution of diisobutylaluminum hydride in toluene. After completion of the addition, the reaction mixture was warmed to −10° C., stirred at this temperature for a further 30 minutes, poured into 100 ml of 0.2N sulphuric acid and extracted twice with 50 ml of methylene chloride each time. The organic phases were washed with 50 ml of water, dried over magnesium sulphate and concentrated. The residue (about 850 mg) was dissolved in 30 ml of methylene chloride and treated successively with 0.5 ml of acetic anhydride and 45 mg of 4-(dimethylamino)pyridine. The reaction mixture was stirred at room temperature for 1 hour, then poured into 50 ml of saturated, aqueous copper sulphate solution and extracted twice with 50 ml of methylene chloride each time. The organic phases were washed twice with 50 ml of water each time, dried over magnesium sulphate and concentrated. Low pressure chromatography (0.5 bar) of the residue (0.95 g) on silica gel with ethyl acetate/petroleum ether (vol. 1:9) gave 720 mg (71%) of p-[trans-4-(3-acetoxy-trans-1-propenyl)cyclohexyl]benzaldehyde; purity 99.9%, Rf-value (ethyl acetate/petroleum ether, vol. 1:9) 0.31.

(e) A solution of 513 mg of hydroxylammonium chloride in 5 ml of water was placed while gassing with argon in a sulphonation flask provided with a mechanical stirrer and treated at room temperature with a solution of 2.0 g of p-[trans-4-(3-acetoxy-trans-1-propenyl)cyclohexyl]benzaldehyde in 10 ml of pyridine. The reaction mixture was stirred for 1 hour and then treated successively with 350 mg of copper sulphate pentahydrate and a solution of 2.1 ml of triethylamine in 10 ml of methylene chloride. After the initially inky blue colour of the copper-pyridine complex had turned olive-green, a solution of 1.74 g of dicyclohexylcarbodiimide in 20 ml of methylene chloride was added. The mixture was subsequently stirred at room temperature for another 3 hours and then filtered. The filtrate was poured into 100 ml of water and extracted three times with 100 ml of methylene chloride each time. The organic phases were washed twice with 50 ml of water each time, dried over magnesium sulphate and concentrated. Low-pressure chromatography (0.5 bar) of the residue (2.75 g) on silica gel with toluene/ethyl acetate (vol. 9:1) gave 2.26 g (114%) of p-[trans-4-(3-acetoxy-trans-1-propenyl)cyclohexyl]benzonitrile as colourless crystals which still contained some dicyclohexylcarbodiimide as the sole impurity. This material was processed without additional purification. Rf-value (toluene/ethyl acetate vol. 9:1) 0.33.

The following compound was prepared in an analogous manner:

p-[Trans-4-(trans-1-butenyl)cyclohexyl]benzonitrile, m.p. (C—N) 44.2° C., cl.p. (N—I) 49.5° C.

EXAMPLE 4

A mixture of 3.8 g of 4-(p-cyanophenyl)cyclohexanecarboxaldehyde (prepared according to Example 3), 10.3 g of propyltriphenylphosphonium bromide and 12.3 g of potassium carbonate in 200 ml of dioxan was heated to reflux for 25 hours while gassing with argon in a round flask provided with a reflux condenser. The cooled reaction mixture was subsequently filtered and concentrated. The residue was taken up in 150 ml of water and extracted three times with 150 ml of diethyl ether each time. The organic phases were washed twice with 100 ml of water each time, dried over magnesium sulphate and concentrated. Low-pressure chromatography (0.5 bar) of the residue (10.5 g) with ethyl acetate/petroleum ether (vol. 3:97) gave 2.35 g (55%) of a colourless, semi-crystalline mass which, according to analysis by gas chromatography, consisted of 80.3 wt.% of p-[trans-4-(cis-1-butenyl)cyclohexyl]benzonitrile, 17.5 wt.% of p-[trans-4-(trans-1-butenyl)cyclohexyl]benzonitrile and 2.2 wt.% of p-[cis-4-(cis-1-butenyl)cyclohexyl]benzonitrile. By additional low-pressure chromatography (0.5 bar) of this material on silica gel coated with 10% silver nitrate using ethyl acetate/petroleum ether (vol. 3:97) and by subsequent crystallization from methanol at −78° C. there could be isolated pure p-[trans-4-(trans-1-butenyl)cyclohexyl]benzonitrile; m.p. (C—N) 44.2° C., cl.p. (N—I) 49.5° C.

EXAMPLE 5

A suspension of 2.51 g of methyltriphenylphosphonium bromide in 80 ml of absolute tetrahydrofuran was placed at −20° C. while gassing with argon in a sulphonation flask provided with a dropping funnel and a thermometer and treated with 7.6 ml of an about 0.8M solution of butyl lithium in hexane. After stirring at −20° C. for 30 minutes, a solution of 1.0 g of trans-4-(p- cyanophenyl)cyclohexanecarboxaldehyde in 10 ml of absolute tetrahydrofuran was added dropwise at −20° C. within 5 minutes to the yellow reaction mixture, whereby the yellow colour disappeared. The mixture was now stirred at −20° C. for a further 30 minutes and then poured into 100 ml of water and extracted three times with 100 ml of diethyl ether each time. The organic phases were washed twice with 100 ml of water each time, dried over magnesium sulphate and concentrated. Low-pressure chromatography (0.5 bar) of the residue (2.3 g) on silica gel with ethyl acetate/petroleum ether (vol. 3:97) gave 897 mg (91%) of p-(trans-4-vinylcyclohexyl)benzonitrile as colourless crystals; purity 99.4%. By additional crystallization from 22 ml of methanol there was obtained p-(trans-4-vinylcyclohexyl)benzonitrile in a purity of 99.95%; m.p. (C—I) 56.4° C., cl.p. 28.5° C.

EXAMPLE 6

A suspension of 3.6 g of butyltriphenylphosphonium bromide in 40 ml of t-butyl methyl ether was placed at room temperature while gassing with argon in a sulphonation flask provided with a thermometer, a mechanical stirrer, a dropping funnel and a solid substance addition tube, treated with 1.01 g of potassium t-butylate and stirred at room temperature for a further 1 hour. The deep orange, heterogeneous reaction mixture was subsequently cooled to −60° C. and treated within 15 minutes with a solution of 1.28 g of trans-4-(p-cyanophenyl)cyclohexanecarboxaldehyde in 10 ml of t-butyl methyl ether. The reaction mixture was stirred for a further 60 minutes while warming slowly to −30° C., then poured into 100 ml of water and extracted three times with 50 ml of diethyl ether each time. The organic phases were washed once with 50 ml of water, dried over magnesium sulphate and concentrated. Low-pressure chromatography (0.5 bar) of the residue (3.45 g) on silica gel with ethyl acetate/petroleum ether (vol. 3:97) gave 1.52 g (99%) of p-[trans-4-(1-pentenyl)cyclohexyl]benzonitrile (trans-1-pentenyl/cis-1-pentenyl ratio about 5:95) as a colourless oil; Rf-value (ethyl acetate/petroleum ether, vol. 3:97) 0.19.

EXAMPLE 7

A mixture of 3.79 g of p-[trans-4-(1-hexenyl)cyclohexyl]benzonitrile (prepared in a manner analogous to Example 6: trans-1-hexenyl/cis-1-hexenyl ratio about 5:95) and 758 mg of benzenesulphinic acid in 50 ml of 1,4-dioxan was boiled under reflux for 15 hours while gassing with argon in a round flask provided with a magnetic stirrer and a reflux condenser. A further 379 mg of benzenesulphinic acid were subsequently added and the mixture was heated to reflux for a further 4 hours. The cooled reaction mixture was then poured into 50 ml of IN sodium hydroxide solution and extracted three times with 100 ml of hexane each time. The organic phases were washed twice with 50 ml of water each time, dried over magnesium sulphate and concentrated. Three-fold crystallization of the quantitatively obtained, equilibrated olefine mixture (trans-1-hexenyl/cis-1-hexenyl ratio 80.4:19.6) from methanol finally gave 1.74 g (46%) of p-[trans-4-(trans-1-hexenyl)cyclohexyl]benzonitrile (containing 0.3% of cis-1-hexenyl isomer) of melting point (C—N) 14.3° C. and cl.p. (N—I) 39.5° C. The mother liquors were not worked-up. However, if desired, these can be again equilibrated and the equilibrated mixture can be subjected to crystallization.

The following compounds were prepared in an analogous manner:

p-[Trans-4-(trans-1-propenyl)cyclohexyl]benzonitrile; m.p. (C—N) 66.3° C., cl.p. (N—I) 73.0° C., p-[trans-4-(trans-1-butenyl)cyclohexyl)benzonitrile; m.p. (C—N) 45.1° C., cl.p. (N—I) 51.8° C., p-[trans-4-(trans-1-pentenyl)cyclohexyl]benzonitrile; m.p. (C—N) 15.6° C., cl.p. (N—I) 58.5° C., p-[trans-4-(trans-1-heptenyl)cyclohexyl]benzonitrile; m.p. (C—N) 17.9° C., cl.p. (N—I) 49.2° C.

EXAMPLE 8

A mixture of 2.75 g of p-[trans-4-(erythro-1,2-dibromopentyl)cyclohexyl]benzonitrile and 20 ml of glacial acetic acid was treated at room temperature with 2.42 g of zinc powder while gassing with argon in a sulphonation flask provided with a mechanical stirrer and a thermometer and then stirred for 2 hours, whereby the mixture warmed to 33° C. and the educt gradually passed into solution. The reaction mixture was subsequently poured into 100 ml of water and extracted three times with 100 ml of petroleum ether each time. The organic phases were washed twice with 100 ml of water each time and once with 50 ml of saturated sodium hydrogen carbonate solution, dried over magnesium sulphate and concentrated. There were thus obtained 1.43 g (99%) of p-[trans-4-(trans-1-pentenyl)cyclohexyl]benzonitrile in a purity of 99.5%; m.p. (C—N) 15.6° C., cl.p. (N—I) 58.5° C.

The p-[trans-4-(erythro-1,2-dibromopentyl)cyclohexyl]benzonitrile used as the starting material was prepared as follows:

(a) A mixture of 1.51 g of 90% m-chloroperbenzoic acid and 3.0 g of powdered potassium carbonate in 60 ml of methylene chloride was placed at 0° C. while gassing with argon in a sulphonation flask provided with a thermometer, a dropping funnel and a mechanical stirrer and treated within 15 minutes with a solution of 2.0 g of p-[trans-4-(1-pentenyl)cyclohexyl]benzonitrile (prepared according to Example 6; trans-1-pentenyl/cis-1-pentenyl ratio about 5:95) in 20 ml of methylene chloride. The cooling bath was subsequently removed and the reaction mixture was treated after a total of 75 minutes and 105 minutes with in each case a further 0.75 g of 90% m-chloroperbenzoic acid. The reaction mixture was stirred at room temperature for a further 60 minutes, then poured into 50 ml of 10% (wt./vol.) sodium thiosulphate solution and extracted three times with 100 ml of methylene chloride each time. The organic phases were washed with 50 ml of saturated sodium hydrogen carbonate solution, dried over magnesium sulphate and concentrated. There were thus obtained 2.1 g (98%) of p-[trans-4-(1,2-epoxypentyl)cyclohexyl]benzonitrile (trans-1,2-epoxypentyl/cis-1,2-epoxypentyl ratio about 5.95) as a colourless oil: Rf-values (ethyl acetate/petroleum ether, vol. 10:90): trans-1,2-epoxypentyl isomer 0.17, cis-1,2-epoxypentyl isomer 0.14.

(b) A solution of 2.46 g of triphenylphoshine in 30 ml of methylene chloride was placed at 0° C. while gassing with argon in a round flask provided with a dropping funnel and treated dropwise with an about 1M solution of bromine in methylene chloride until a faint yellow colour remained. The solution was subsequently concentrated cautiously on a rotary evaporator and then dried in a high vacuum. The crystalline residue obtained was suspended in 30 ml of benzene, treated with a solution of 2.1 g of p-[trans-4-(1,2-epoxypentyl)cyclohexyl]- benzonitrile in 10 ml of benzene and heated to reflux for 3 hours. Filtration of the warm solution on silica gel with toluene gave 3.0 g of crystalline crude product which, after low-pressure chromatography (0.5 bar) on silica gel with hexane/toluene (vol. 1:1), yielded 2.61 g (81%) of almost pure p-[trans-4-(erythro-1,2-dibromopentyl)cyclohexyl]benzonitrile as colourless crystals. By recrystallization from 90 ml of petroleum ether/ethyl acetate (vol. 2:1) there were finally obtained 2.09 g (65%) of very pure erythro dibromide; m.p. 140.9° C.

The following compounds were prepared in an analogous manner:

p-[Trans-4-(trans-1-propenyl)cyclohexyl]benzonitrile; m.p. (C—N) 66.3° C., cl.p. (N—I) 73.0° C., p-[trans-4-(trans-1-butenyl)cyclohexyl]benzonitrile; m.p. (C—N) 45.1° C., cl.p. (N—I) 51.8° C., p-[trans-4-(trans-1-hexenyl)cyclohexyl]benzonitrile; m.p. (C—N) 14.4° C., cl.p. (N—I) 39.2° C.

p-trans-4-(trans-1-heptenyl)cyclohexyl]benzonitrile; m.p. (C—N) 17.9° C., cl.p. (N—I) 49.2° C.

EXAMPLE 9

In an analogous manner to Examples 3, 5, 6 and 8, 4-[2-(p-cyanophenyl)ethyl]cyclohexanone was converted into trans-4-[2-(p-cyanophenyl)ethyl]cyclohexanecarboxaldehyde and the latter was converted into p-[2-(trans-4-(trans-1-alkenyl)cyclohexyl)ethyl]benzonitriles.

The 4-[2-(p-cyanophenyl)ethyl]cyclohexanone used as the starting material was prepared as follows:

(a) 149 g of methoxymethyl-triphenylphosphonium chloride and 860 ml of t-butyl methyl ether were placed in a sulphonation flask at room temperature while stirring and gassing with nitrogen, the suspension was cooled to −10° C. and treated within 10 minutes with 51.6 g of potassium t-butylate. The suspension was stirred at −10° C. to 0° C. for a further 30 minutes and then treated dropwise within 45 minutes at 0° C. with a solution of 47.3 g of 4,4-ethylenedioxycyclohexanone in 720 ml of tetrahydrofuran. The orange suspension was stirred at room temperature for a further 2 hours, then poured into 5 l of hexane, stirred for 10 minutes and suction filtered. The filtrate was concentrated in vacuo and the resulting yellow-brownish oil (104.1 g) was treated with 500 ml of hexane and suction filtered. The filtrate was concentrated in vacuo, 61.7 g of a yellow brownish oil being obtained. Chromatographic separation of this crude product on silica gel with methylene chloride/acetone (vol. 98:2 and 95:5) finally gave 53.5 g of 1,1-ethylenedioxy-4-(methoxymethylene)cyclohexane as a colourless oil.

(b) A mixture of 28.2 g of 1,1-ethylenedioxy-4-(methoxymethylene)cyclohexane, 770 ml of glacial acetic acid and 385 ml of water was heated to reflux for 1 hour while gassing with nitrogen in a round flask. Thereafter the yellowish clear solution was cooled to room temperature, diluted with 800 ml of water and extracted three times with 700 ml of methylene chloride each time. The organic phases were washed twice with 500 ml of 10% (wt./vol,) sodium carbonate solution each time, dried over sodium sulphate, filtered and concentrated. Chromatographic separation of the resulting brownish liquid (18.5 g) on silica gel with methylene chloride as the eluent finally gave 16.7 g of 4-formylcyclohexanone as a brownish liquid.

(c) 63.3 g of p-cyanobenzyl-triphenylphosphonium chloride, 17.2 g of potassium t-butylate and 195 ml of ethylene glycol dimethyl ether were placed while stirring and gassing with nitrogen in a sulphonation flask, whereby the internal temperature rose to 44° C. The brown suspension was cooled to 0° C. and treated within 2 minutes with a solution of 16.7 g of 4-formylcyclohexanone in 100 ml of ethylene glycol dimethyl ether. The cooling bath was then removed and the mixture was stirred at room temperature for a further 3.5 hours. The suspension was subsequently poured into 500 ml of water and extracted three times with 600 ml of methylene chloride each time. The organic phases were washed twice with 500 ml of 10% (wt./vol.) sodium chloride solution each time, dried over sodium sulphate, filtered and concentrated, there being obtained 76.9 g of a brownish paste. Chromatographic separation of this crude product on silica gel with methylene chloride as the eluent gave 33.0 g of 4-[2-(p-cyanophenyl)vinyl]cyclohexanone as a yellow-brownish oil.

(d) A mixture of 33.0 g of 4-[2-(p-cyanophenyl)vinyl]cycyclohexanone, 520 ml of toluene, 260 ml of ethanol and 3.2 g of palladium/carbon (5%) was placed at room temperature in a round flask provided with a magnetic stirrer and the mixture was hydrogenated until the hydrogen uptake came to a standstill. The black suspension was subsequently suction filtered (rinsing with toluene) and the filtrate was concentrated in vacuo. The resulting, slightly turbid, yellowish oil (34.1 g) was separated by chromatography on silica gel. Elution with methylene chloride/hexane (vol. 1:1), methylene chloride/hexane (vol. 8:2) and methylene chloride yielded 25.6 g of a yellowish oil which was crystallized from t-butyl methyl ether. There were thus obtained 22.6 g of 4-[2-(p-cyanophenyl)ethyl]cyclohexanone as colourless crystals of melting point 62.5°-64.3° C.

The following compounds were prepared in an analogous manner:

p-[2-(Trans-4-(trans-1-propenyl)cyclohexyl)ethyl]benzonitrile; m.p. (C—I) 61.3° C., cl.p. (N—I) 54.2° C., p-[2-(trans-4-(trans-1-butenyl)cyclohexyl)ethyl]benzonitrile; m.p. (C—I) 42.6° C., cl.p. (N—I) 39.7° C., p-[2-(trans-4-(trans-1-pentenyl)cyclohexyl)ethyl]benzonitrile; m.p. (C—N) 25.1° C., cl.p. (N—I) 47.5° C., p-[2-(trans-4-(trans-1-hexenyl)cyclohexyl)ethyl]benzonitrile; m.p. (C—N) 16.8° C. and 19.7° C. (2 modifications), cl.p. (N—I) 34.6° C., p-[2-(trans-4-(trans-1-heptenyl)cyclohexyl)ethyl]benzonitrile; m.p. (C—N) 31.6° C., cl.p. (N—I) 43.6° C.

EXAMPLE 10

A suspension of 6.64 g of methyltriphenylphosphonium bromide in 80 ml of t-butyl methyl ether was treated with 2.12 g of solid potassium t-butylate at −10° C. within 3 minutes while gassing with argon in a sulphonation flask provided with a mechanical stirrer. The mixture was stirred at room temperature for another 1 hour, then treated at 0° C. within 5 minutes with a solution of 3.0 g of 3-[trans-4-(p-cyanophenyl)cyclohexyl]propionaldehyde in 20 ml of t-butyl methyl ether and stirred at room temperature for a further 15 minutes. The reaction mixture was subsequently partitioned three times in diethyl ether/water. The organic extracts were washed twice with water, dried over magnesium sulphate, filtered and evaporated. In order to separate triphenylphosphine oxide, the residue was dissolved in ethyl acetate and the solution was diluted with petroleum ether, filtered and evaporated. Chromatographic separation of the resulting, pale brown oil (4.38 g) on silica gel with ethyl acetate/petroleum ether (vol. 3:97)

gave 2.83 g of white crystals. Recrystallization from methanol and working-up of the mother liquor finally gave a total of 2.116 g of p-[trans-4-(3-butenyl)cyclohexyl]benzonitrile as white crystals; m.p. (C—N) 49.5° C., cl.p. (N—I) 52.5° C.

The 3-[trans-4-(p-cyanophenyl)cyclohexyl]propionaldehyde used as the starting material was prepared as follows:

(a) A suspension of 29.0 g of methoxymethyl-triphenylphosphonium chloride in 200 ml of t-butyl methyl ether was treated with 9.7 g of potassium t-butylate at −10° C. within 3 minutes while gassing with argon in a sulphonation flask provided with a mechanical stirrer. The orange suspension was stirred at about 0° C. for 1 hour, then treated dropwise at −10° C. within 10 minutes with a solution of 12.0 g of trans-4-(p-cyanophenyl)cyclohexanecarboxaldehyde in 90 ml of t-butyl methyl ether and stirred at 0° C. for a further 45 minutes. The reaction mixture was subsequently partitioned three times in diethyl ether/water. The organic extracts were washed twice with water, dried over magnesium sulphate, filtered and evaporated. In order to separate triphenylphosphine oxide, the residue was dissolved in ethyl acetate and the solution was diluted with petroleum ether, filtered and evaporated. Chromatographic separation of the yellowish, crystalline residue (16.3 g) on silica gel with ethyl acetate/petroleum ether (vol. 5:95) gave 10.1 g (74%) of p-[trans-4-(2-methoxyvinyl)cyclohexyl]benzonitrile as white crystals.

(b) A solution of 10.1 g of p-[trans-4-(2-methoxyvinyl)cyclohexyl]benzonitrile in 200 ml of tetrahydrofuran/2N hydrochloric acid (vol. 4:1) was heated to reflux for 1 hour while stirring. The reaction mixture was subsequently partitioned three times in diethyl ether/water. The organic extracts were washed twice with water, dried over magnesium sulphate, filtered and evaporated, there being obtained 9.8 g of 2-[trans-4-(p-cyanophenyl)cyclohexyl]acetaldehyde as a light yellowish, crystalline residue.

(c) A suspension of 22.2 g of methoxymethyl-triphenylphosphonium chloride in 150 ml of t-butylmethyl ether was treated with 7.4 g of solid potassium t-butylate at 0° C. within 3 minutes while gassing with argon in a sulphonation flask provided with a mechanical stirrer. The orange suspension was stirred at 0° C. for 1 hour and then treated dropwise within 10 minutes with a solution of 9.8 g of 2-[trans-4-(p-cyclophenyl)cyclohexyl]acetaldehyde in 100 ml of tetrahydrofuran. Subsequently, the suspension was left to warm slowly to room temperature while stirring. After 15 hours, the suspension was partitioned three times in diethyl ether/water. The organic extracts were washed twice with water, dried over magnesium sulphate, filtered and evaporated. In order to separate triphenylphosphine oxide, the residue was dissolved in ethyl acetate and the solution was diluted with petroleum ether, filtered and evaporated. Chromatographic separation of the resulting, yellowish oil (13.7 g) on silica gel with ethyl acetate/petroleum ether (vol. 5:95) gave 10.5 g (96%) of p-[trans-4-(3-methoxy-2-propenyl)cyclohexyl]benzonitrile as a colourless oil.

(d) A solution of 10.5 g of p-[trans-4-(3-methoxy-2-propenyl)cyclohexyl]benzonitrile in 200 ml of tetrahydrofuran/2N hydrochloric acid (vol. 4:1) was heated to reflux for 45 minutes while stirring. The reaction mixture was then partitioned three times in diethyl ether/water. The organic extracts were washed twice with water, dried over magnesium sulphate, filtered and evaporated. Chromatographic separation of the white, crystalline residue (9.9 g) on silica gel with ethyl acetate/petroleum ether (vol. 10:90 and 30:70) finally gave 9.4 g (95%) of 3-[trans-4-(p-cyanophenyl)cyclohexyl]propionaldehyde as white crystals.

EXAMPLE 11

A solution of 9.54 g of p-[trans-4-(erythro-3,4-dibromopentyl)cyclohexyl]benzonitrile in 100 ml of glacial acetic acid was treated with 9.8 g of zinc powder while gassing with argon in a round flask provided with a magnetic stirrer. The mixture was stirred at room temperature for 30 minutes and then partitioned three times in petroleum ether/water. The organic extracts were washed twice with water, dried over magnesium sulphate, filtered and concentrated. Chromatographic separation of the oily residue (5.56 g) on silica gel coated with silver nitrate (prepared by suspending 300 g of silica gel in 500 ml of a 0.2M solution of silver nitrate in acetonitrile, subsequently filtering and drying the residue) using diethyl ether/hexane (vol. 1:9) as the eluent gave 3.2 g of crude product as white crystals. After recrystallization from 80 ml of methanol, 1.65 g (28%) of p-[trans-4-(trans-3-pentenyl)cyclohexyl]benzonitrile were obtained as white crystals. The mother liquor and the impure fractions from the chromatographic separation were combined and again purified on silica gel coated with silver nitrate using diethyl ether/hexane (vol. 1:9) as the eluent. Recrystallization of the resulting, crystalline product (1.5 g) from 40 ml of methanol gave a further 0.65 g of p-[trans-4- -(trans-3-pentenyl)cyclohexyl]benzonitrile as white crystals: m.p. (C—N) 59.8° C., cl.p. (N—I) 73.7° C.

The p-[trans-4-(erythro-3,4-dibromopentyl)cyclohexyl]benzonitrile used as the starting material was prepared as follows:

(a) A suspension of 14.8 g of ethyltriphenylphosphonium bromide in 150 ml of t-butyl methyl ether was treated with 4.54 g of solid potassium t-butylate at −10° C. within 5 minutes while gassing with argon in a sulphonation flask provided with a mechanical stirrer. The suspension was stirred at room temperature for 1 hour, then treated dropwise at 0° C. over a period of 5 minutes with a solution of 6.4 g of 3-[trans-4-(p-cyanophenyl)cyclohexyl]propionaldehyde in 40 ml of t-butyl methyl ether and stirred at room temperature for another 15 hours. The reaction mixture was subsequently partitioned three times in diethyl ether/water. The organic extracts were washed twice with water, dried over magnesium sulphate, filtered and concentrated. In order to separate triphenylphosphine oxide, the residue was dissolved in ethyl acetate and the solution was diluted with petroleum ether, filtered and concentrated. Chromatographic separation of the resulting, yellowish oil (8.55 g) on silica gel with ethyl acetate/petroleum ether (vol. 3:97) gave 5.93 g (89%) of p-[trans-4-(3-pentenyl)cyclohexyl]benzonitrile as white crystals.

(b) A solution of 4.49 g of 90% m-chloroperbenzoic acid in 100 ml of methylene chloride was treated with 11.3 g of powdered potassium carbonate. The mixture was treated dropwise at 0° C. within 5 minutes with a solution of 5.93 g of p-[trans-4-(3-pentenyl)cyclohexyl]benzonitrile in 20 ml of methylene chloride and stirred at room temperature for 2 hours. The mixture was subsequently treated with another 4.49 g of 90% m-chloroperbenzoic acid and the resulting mixture was stirred further. After a total of 70 hours, the reaction mixture was partitioned three times in methylene chloride/10% sodium thiosulphate solution. The organic extracts were washed with sodium thiosulphate solution and water, dried over magnesium sulphate, filtered and concentrated. Chromatographic separation of the resulting, light yellowish oil (6.3 g) on silica gel with ethyl acetate/petroleum ether (vol. 10:90) gave 6.27 g (99.5%) of p-[trans-4-(3,4-epoxypentyl)cyclohexyl]benzonitrile as a colourless oil.

(c) A solution of 7.4 g of triphenylphosphine in 80 ml of methylene chloride was treated dropwise with a solution of 1.5 ml of bromine in 20 ml of methylene chloride while gassing with argon until the yellow colour remained. The mixture was then evaporated on a rotary evaporator and the residue was dried in a high vacuum for 1 hour. The yellow crystalline residue was suspended in 120 ml of benzene. The suspension was treated with 6.27 g of p-[trans-4-(3,4-epoxypentyl)cyclohexyl]benzonitrile and heated to reflux while stirring for 1 hour. The reaction mixture was subsequently filtered on silica gel using toluene as the eluent. Concentration of the product-containing fractions finally gave 9.54 g (99.1%) of p-[trans-4-(erythro-3,4-dibromopentyl)cyclohexyl]benzonitrile as a light brownish oil.

EXAMPLE 12

A mixture of 1.00 g of 2-(trans-1-pentenyl)-1,3-propanediol, 1.11 g of p-butoxybenzaldehyde, 3 drops of 2N sulphuric acid and 40 ml of toluene was heated to reflux for 2 hours with the separation of water. The mixture was subsequently treated with 7 drops of triethylamine, left to cool, washed with 5 ml of saturated sodium hydrogen carbonate solution and three times with 10 ml of water each time, dried over sodium carbonate, filtered and concen-trated. The semi-crystalline residue (1.86 g) was chro-matographed on silica gel with hexane/diethyl ether (vol. 97:3). The product-containing fractions were pooled (0.99 g) and recrystallized twice from hexane at −25° C. There was obtained 0.44 g of pure trans-2-(p-butoxyphenyl)-5-(trans-1-pentenyl)-m-dioxan; m.p. (C—N) 60.6° C., cl.p. (N—I) 61.9° C.

The 2-(trans-1-pentenyl)-1,3-propanediol used as the starting material was prepared as follows:

A solution of 16.1 g of diethyl 2-(trans-1-pentenyl)-malonate (Tetrahedron Lett. 1979, 861) in 75 ml of tetrahydrofuran was added dropwide to a suspension of 5.3 g of lithium aluminum hydride in 200 ml of dry tetrahydrofuran at 5° C. within 1 hour while stirring in an inert gas atmosphere. The mixture was stirred at room temperature for a further 3.5 hours and then successively treated dropwise with 15 ml of acetone and 20 ml of saturated sodium hydrogen carbonate solution. The reaction mixture was filtered, the filtrate was concentrated and the residue (8.2 g) was distilled in a bulb-tube at 150° C./about 1 Torr. There were thus obtained 6.5 g of 2-(trans-1-pentenyl)-1,3-propanediol as a colourles oil.

The following compounds were prepared in an analogous manner.

p-[Trans-5-(trans-1-propenyl)-m-dioxan-2-yl]benzonitrile; m.p. (C—I) 97° C., cl.p. (N—I) 73° C., p-[trans-5-(trans-1-butenyl)-m-dioxan-2-yl]benzonitrile; m.p. (C—I) 92.2° C., p-[trans-5-(trans-1-pentenyl)-m-dioxan-2-yl]benzonitrile; m.p. (C—I) 67.2° C. cl.p. (N—I) 59.1° C., p-[trans-5-(trans-1-hexenyl)-m-dioxan-2-yl]benzonitrile; m.p. (C—I) 50.5° C., cl.p. (N—I) 37.0° C., p-[trans-5-(trans-1-heptenyl)-m-dioxan-2yl]benzonitrile; m.p. (C—I) 49.3° C., cl.p. (N—I) 49.2° C.

We claim:

1. A compound of the formula:

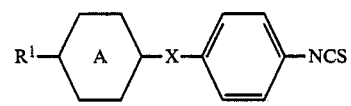

wherein X is a single covalent bond, —CH$_2$CH$_2$—, 1,4-phenylene, a 2,5-disubstituted pyrimidine ring or a group of the formula:

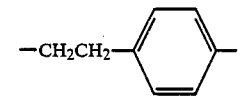

ring A is trans-1,4-cyclohexylene or, when X is a single covalent bond, ring A may also be 1,4-phenylene, a 2,5-disubstituted pyrimidine ring or a trans-2,5-disubstituted m-dioxane ring; and R$^1$ is a straight-chain trans-1-alkenyl having 2 to 12 carbon atoms or a straight-chain trans-3-alkenyl having 4 to 12 carbon atoms or, when X is —CH$_2$CH$_2$—, 1,4-phenylene, or a 2,5-disubstituted pyrimidine ring or when ring A is a 2,5-disubstituted pyrimidine ring, R$^1$ may also be straight-chain alkyl with 1 to 12 carbon atoms; and one of the benzene rings may have a lateral fluorine substituent.

2. The compound of claim 1, wherein X is a single covalent bond, 1,4-phenylene or a 2,5-disubstituted pyrimidine ring.

3. The compound of claim 1 wherein X is a single covalent bond; ring A is a 2,5-disubstituted pyrimidine ring; and R$^1$ is straight-chain trans-1-alkenyl having 2 to 12 carbon atoms, straight-chain trans-3-alkenyl having 4 to 12 carbon atoms, or straight-chain alkyl having 1 to 12 carbon atoms.

4. The compound of claim 1 wherein X is —CH$_2$CH$_2$—; ring A is trans-1,4-cyclohexylene; and R$^1$ is straight-chain trans-1-alkenyl having 2 to 12 carbon atoms, straight-chain trans-3-alkenyl having 4 to 12 carbon atoms or straight-chain alkyl having 1 to 12 carbon atoms.

5. The compound of claim 1 wherein X is a single covalent bond; ring A is trans-1,4-cyclohexylene; and R$^1$ is straight-chain trans-1-alkenyl having 2 to 12 carbon atoms or straight-chain trans-3-alkenyl having 4 to 12 carbon atoms.

6. The compound of claim 1 wherein R$^1$ is straight-chain trans-1-alkenyl having 2 to 7 carbon atoms or straight-chain trans-3-alkenyl having 4 to 7 carbon atoms.

7. The compound of claim 1 wherein R$^1$ is straight-chain alkyl having 1 to 7 carbon atoms.

8. A liquid crystalline mixture having at least 2 components, wherein at least one component is a compound of the formula:

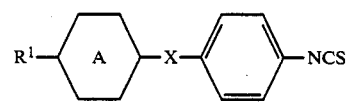

wherein X is a single covalent bond, —CH₂CH₂—, 1,4-phenylene, a 2,5-disubstituted pyrimidine ring or a group of the formula:

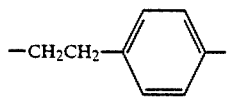
                                                                    IA ring A is trans-1,4-cyclohexylene or, when X is a single covalent bond, ring A may also be 1,4-phenylene, a 2,5-disubstituted pyrimidine ring or a trans-2,5-disubstituted m-dioxane ring; and $R^1$ is a straight-chain trans-1-alkenyl having 2 to 12 carbon atoms or a straight-chain trans-3-alkenyl having 4 to 12 carbon atoms or, when X is —CH₂CH₂—, 1,4-phenylene, or a 2,5-disubstituted pyrimidine ring or when ring A is a 2,5-disubstituted pyrimidine ring, $R^1$ may also be straight-chain alkyl with 1 to 12 carbon atoms; and one of the benzene rings may have a lateral fluorine substituent.

9. An electro-optical cell comprising
   (a) two plate means
   (b) a liquid crystal means disposed between two plate means and including a compound of the formula:

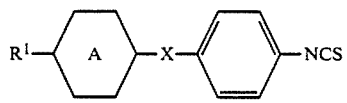
                                                                    I wherein X is a single covalent bond, —CH₂CH₂—, 1,4-phenylene, a 2,5-disubstituted pyrimidine ring or a group of the formula:

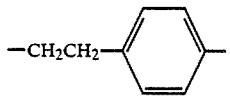
                                                                    IA ring A is trans-1,4-cyclohexylene or, when X is a single covalent bond, ring A may also be 1,4-phenylene, a 2,5-disubstituted pyrimidine ring or a trans-2,5-disubstituted m-dioxane ring; and $R^1$ is a straight-chain trans-1-alkenyl having 2 to 12 carbon atoms or a straight-chain trans-3-alkenyl having 4 to 12 carbon atoms or, when X is —CH₂CH₂—, 1,4-phenylene, or a 2,5-disubstituted pyrimidine ring or when ring A is a 2,5-disubstituted pyrimidine ring, $R^1$ may also be straight-chain alkyl with 1 to 12 carbon atoms; and one of the benzene rings may have a lateral fluorine substituent, and
   (c) means for applying an electrical potential to said plate means.

* * * * *